United States Patent
Barr et al.

(10) Patent No.: US 6,277,590 B1
(45) Date of Patent: *Aug. 21, 2001

(54) COMPOSITIONS AND METHODS FOR PACE 4 AND 4.1 GENE AND POLYPEPTIDES IN CELLS

(75) Inventors: Philip J. Barr, Berkeley; Michael C. Kiefer, Clayton, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/236,503

(22) Filed: Jan. 25, 1999

Related U.S. Application Data

(60) Continuation of application No. 08/447,642, filed on May 23, 1995, now Pat. No. 5,989,890, which is a division of application No. 08/284,941, filed on Aug. 2, 1994, now Pat. No. 5,863,756, which is a continuation of application No. 07/848,629, filed on Mar. 9, 1992, now abandoned.

(51) Int. Cl.$^7$ .............................. C12P 21/06; C12N 9/64; C12N 15/09; C12N 15/57
(52) U.S. Cl. ................... 435/68.1; 435/226; 435/252.3; 435/254.11; 435/254.2; 435/320.1; 435/69.4; 435/70.1; 435/70.3; 435/71.1; 435/71.2; 435/325; 435/348; 435/358; 536/232
(58) Field of Search ................................ 435/69.1, 226, 435/252.3, 254.11, 254.2, 320.1, 68.1, 69.4, 70.1, 70.3, 71.1, 71.2, 325, 348, 358; 536/23.2

(56) References Cited

U.S. PATENT DOCUMENTS

| | | | |
|---|---|---|---|
| 4,973,668 | 11/1990 | Jallat | 530/380 |
| 5,093,316 | 3/1992 | Lezdey | 514/8 |
| 5,166,134 | 11/1992 | Lezdey | 514/8 |
| 5,217,951 | 6/1993 | Lezdey | 514/8 |

FOREIGN PATENT DOCUMENTS

| WO A 9209698 | 6/1992 | (WO) . |
|---|---|---|

OTHER PUBLICATIONS

Barr P.J. Cell 66:1–3 (1991).
Barr P.J. et al., DNA and Cell Biology 10:(5)319–328 (1991.
Benjannet S. et al., Proc. Natl. Acad. Sci. USA 88:3564–3568 (1991).
Bresnahan, J. et al. J. Cell. Biol. 111:2851–2859 (1990).
Christie D.L. et al., The Journal of Biological Chemistry 266:(24)15679–15683 (1991).
Fuller R.S. et al., Proc. Natl. Acad. Sci. USA 86:1434–1438 (1989).
Fuller R.S. et al., Science 246:482–486 (1989).
Hatsuzawa et al., J. Biol. Chem. 265(36)22075–22078 (Dec. 1990).
Hosaka N. et al., The J. of Biological Chemistry 266:12127–12130 (1991).
Julius D. et al., Cell 36:309–318 (1984).
Misumi Y. et al., The J. of Biological Chemistry 266:(25)16954–16959 (1991).
Mizuno K.et al., Biochemical and Biophysical Research Communications 156:(1)246–254 (1988).
Oweland Van den et al., Nuc. Acid. Res. 18(3):664 (1990).
Roebroek A.J.M. et al., Molec. Biol. Rep. 11:117–125 (1986).
Roebroek A.J.M. et al., The EMBO J. 5:(9)2197–2202 (1986).
Schalken J.A. et al., J. Clin. Invest. 80:1545–1549 (1987).
Seidah et al DNA Cell. Biol. 9:415–424 (1990).
Seidah N.G. et al., Mol. Endo. 5:111–122 (1991).
Shennan K.I.J. et al., The J. of Biological Chemistry 266:(35)24011–24017 (1991).
Smeekens et al. Proc. Natl Acad. Sci. 88:340–344 (1991).
Smeekens S.P. et al., The J. of Biological Chemistry 266:(6)2997–3000 (1990).
Thomas G. et al., Science 214:226–230 Jul. (1988).
Thomas L. et al., Proc. Natl. Acad. Sci. USA 88:5297–5301 (1991).
Wim J.M. van de Ven et al., Molecular Biology Reports 14:265–275 (1990).
Wise et al. Proc. Natl Acad. Sci. 87:9378–9382 (1990).
Bell W.R., Kirk–Othmer Encyclopedia of Chemical Technology, Fourth Edition, 4:333–360 (1992).
Kiefer M.C. et al., DNA and Cell Biology 10:(10)757–769 (1991).
Sesboué et al Clin. Chimica Acta 135:23–33 (1983).

*Primary Examiner*—Rebecca E. Prouty
(74) *Attorney, Agent, or Firm*—Roberta L. Robins; Joseph H. Guth; Robert P. Blackburn

(57) ABSTRACT

Compositions and methods are provided for endopeptidases and their production, and for enhanced efficiencies of processing heterologous precursor polypeptides to mature polypeptides. These compositions and methods utilize recombinant PACE 4 and 4.1, mammalian endopeptidases that are specific for dibasic amino acid sites. Therapeutic compositions and methods employing PACE 4 or 4.1 or their inhibitors are also provided.

30 Claims, 12 Drawing Sheets

Figure 4:
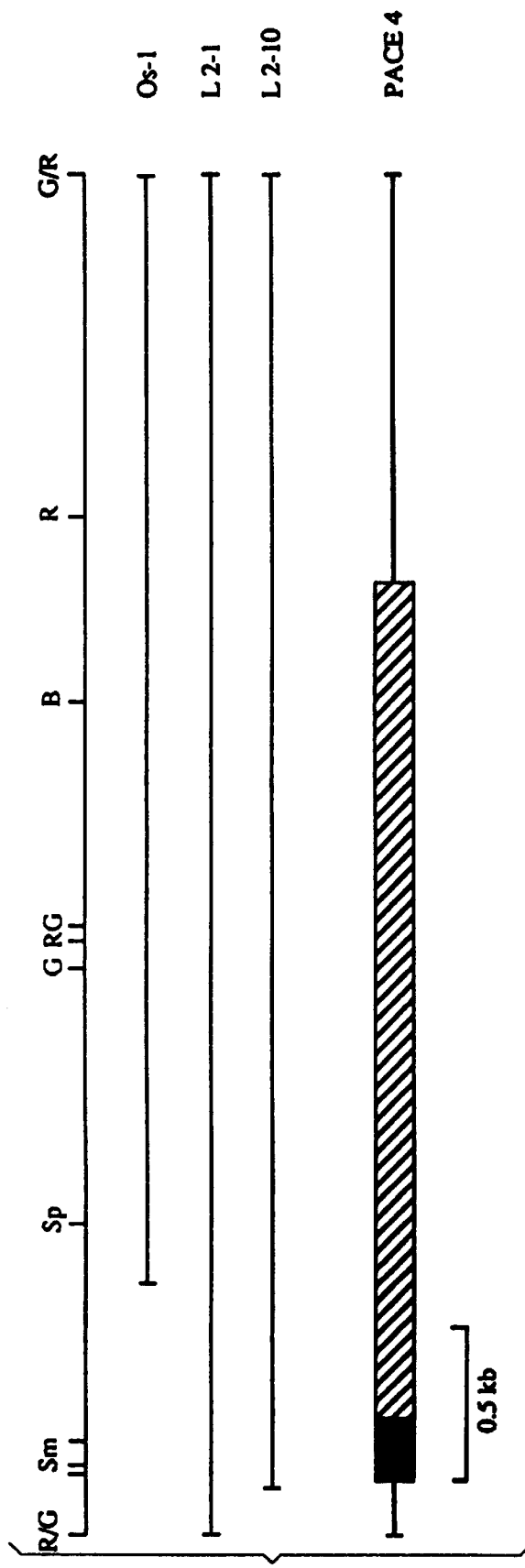

```
         GlyHisLysGlyValAlaAlaValAlaPheTrpTrpThrIleGlyTrpProTrpAsnValAm
GGTCATAAAGGTGCGGGCAGTGGCGTTCTGGTGGTGACCATTGGGTGGCCCTGGAATGTGTAG
GAAGGGGTGTCATGAATTCCTTAAAAGGACTCTCCAAATAGCATTAGTTGTTGTTATTATTAA
CTTAAAGGAACTCTCCAAATAGCTATTTGTTATTATTATTCCGGAAGCTCACAGTGTGTCACAAGAATTT
AAAACGCATGTGCAGGTCACAGAAGTATCCGGAAGCTCACAGTGACATTACGGAAGA
GAACCCTCAGGTCACAGAAGTCTGGGGTCTCCTATAGTTCTCTTTAGCCAGGAGCAATGACGTGTGC
ACACCACCTATACCAATATTTACTCATAGTTCTCTTTAGCCAGGAGCAATGACGTGTGA
CTATAGTCGCAGCTACTAGGAAGTTGAGGCAGGAGGATTGCTTGAGCCAGGAATTGA
GTCTAGCCTGGACAACACAGCAGGACTCCATCTCTTAAAAGGAAACTGTACTACATCTAGTTAATCA
ACTTTTTTGATATGTAGTTACGTATTTTTCTAATGTGCATTAAAACAAATCCATAATTAT
TAGGTTTGATATGTAGTTACGTATTTTTCTAATGTGCATTAAAACAAATCCATAATTAT
TAAAATAAATGTTGTTTGTTTGTGTGCCAAAAAAAAAAA
```

FIG. 3

```
                                          SerHisPheTyrGlyPheGlyLeuValAspAlaAlaGluAla
5'...ggcctgtgtctttttcag TTAGCCATTTCTATGGATTTGGTTTGGTGGACGCAGAAGCT
                        LeuValAlaGluAlaLysLysTrpThrAlaValProSer
                        CTCGTTGTGGAGGCAAAGAAGTGGACAGCAGTGCCATCG
                        GlnHisMetCysValAlaAlaSerAspLysArgPro
                        CAGCACATGTGTGTGGCCGCCTGGACAAGAGACCCAG gtaaggctctgctgt...3'
```

FIG. 7

SEQUENCE LISTING

<160> NUMBER OF SEQ ID NOS: 16

<210> SEQ ID NO 1
<211> LENGTH: 4403
<212> TYPE: DNA
<213> ORGANISM: Homo sapiens
<220> FEATURE:
<221> NAME/KEY: CDS
<222> LOCATION: (170)..(3076)

<400> SEQUENCE: 1

```
cgggaacgcg ccgcggccgc ctcctcctcc ccggctcccg cccgcggcgg tgttggcggc      60
ggcggtggcg gcggcggcgg cgcttccccg gcgcggagcg gctttaaaag gcggcactcc     120
accccccggc gcactcgcag ctcgggcgcc gcgcgagcct gtcgccgct atg cct ccg     178
                                                       Met Pro Pro
                                                         1 cgc gcg ccg cct gcg ccc ggg ccc cgg ccg ccg ccc cgg gcc gcc gcc      226
Arg Ala Pro Pro Ala Pro Gly Pro Arg Pro Pro Pro Arg Ala Ala Ala
          5                  10                  15 gcc acc gac acc gcc gcg ggc gcg ggg ggc gcg ggg ggc gcg ggg ggc      274
Ala Thr Asp Thr Ala Ala Gly Ala Gly Gly Ala Gly Gly Ala Gly Gly
 20                  25                  30                  35 gcc ggc ggg ccc ggg ttc cgg ccg ctc gcg ccg cgt ccc tgg cgc tgg      322
Ala Gly Gly Pro Gly Phe Arg Pro Leu Ala Pro Arg Pro Trp Arg Trp
                 40                  45                  50 ctg ctg ctg ctg gcg ctg cct gcc gcc tgc tcc gcg ccc ccg ccg cgc      370
Leu Leu Leu Leu Ala Leu Pro Ala Ala Cys Ser Ala Pro Pro Pro Arg
             55                  60                  65 ccc gtc tac acc aac cac tgg gcg gtg caa gtg ctg ggc ggc ccg gcc      418
Pro Val Tyr Thr Asn His Trp Ala Val Gln Val Leu Gly Gly Pro Ala
         70                  75                  80 gag gcg gac cgc gtg gcg gcg gcg cac ggc tac ctc aac ttg ggc cag      466
Glu Ala Asp Arg Val Ala Ala Ala His Gly Tyr Leu Asn Leu Gly Gln
 85                  90                  95 att gga aac ctg gaa gat tac tac cat ttt tat cac agc aaa acc ttt      514
Ile Gly Asn Leu Glu Asp Tyr Tyr His Phe Tyr His Ser Lys Thr Phe
100                 105                 110                 115 aaa aga tca acc ttg agt agc aga ggc cct cac acc ttc ctc aga atg      562
Lys Arg Ser Thr Leu Ser Ser Arg Gly Pro His Thr Phe Leu Arg Met
                120                 125                 130 gac ccc cag gtg aaa tgg ctc cag caa cag gaa gtg aaa cga agg gtg      610
Asp Pro Gln Val Lys Trp Leu Gln Gln Gln Glu Val Lys Arg Arg Val
            135                 140                 145 aag aga cag gtg cga agt gac ccg cag gcc ctt tac ttc aac gac ccc      658
Lys Arg Gln Val Arg Ser Asp Pro Gln Ala Leu Tyr Phe Asn Asp Pro
        150                 155                 160 att tgg tcc aac atg tgg tac ctg cat tgt ggc gac aag aac agt cgc      706
Ile Trp Ser Asn Met Trp Tyr Leu His Cys Gly Asp Lys Asn Ser Arg
165                 170                 175 tgc cgg tcg gaa atg aat gtc cag gca gcg tgg aag agg ggc tac aca      754
Cys Arg Ser Glu Met Asn Val Gln Ala Ala Trp Lys Arg Gly Tyr Thr
180                 185                 190                 195 gga aaa aac gtg gtg gtc acc atc ctt gat gat ggc ata gag aga aat      802
Gly Lys Asn Val Val Val Thr Ile Leu Asp Asp Gly Ile Glu Arg Asn
                200                 205                 210 cac cct gac ctg gcc cca aat tat gat tcc tac gcc agc tac gac gtg      850
His Pro Asp Leu Ala Pro Asn Tyr Asp Ser Tyr Ala Ser Tyr Asp Val
            215                 220                 225
```

```
aac ggc aat gat tat gac cca tct cca cga tat gat gcc agc aat gaa    898
Asn Gly Asn Asp Tyr Asp Pro Ser Pro Arg Tyr Asp Ala Ser Asn Glu
        230                 235                 240 aat aaa cac ggc act cgt tgt gcg gga gaa gtt gct gct tca gca aac    946
Asn Lys His Gly Thr Arg Cys Ala Gly Glu Val Ala Ala Ser Ala Asn
245                 250                 255 aat tcc tac tgc atc gtg ggc ata gcg tac aat gcc aaa ata gga ggc    994
Asn Ser Tyr Cys Ile Val Gly Ile Ala Tyr Asn Ala Lys Ile Gly Gly
260                 265                 270                 275 atc cgc atg ctg gac ggc gat gtc aca gat gtg gtc gag gca aag tcg   1042
Ile Arg Met Leu Asp Gly Asp Val Thr Asp Val Val Glu Ala Lys Ser
                280                 285                 290 ctg ggc atc aga ccc aac tac atc gac att tac agt gcc agc tgg ggg   1090
Leu Gly Ile Arg Pro Asn Tyr Ile Asp Ile Tyr Ser Ala Ser Trp Gly
                295                 300                 305 ccg gac gac gac ggc aag acg gtg gac ggg ccc ggc cga ctg gct aag   1138
Pro Asp Asp Asp Gly Lys Thr Val Asp Gly Pro Gly Arg Leu Ala Lys
            310                 315                 320 cag gct ttc gag tat ggc att aaa aag ggc cgg cag ggc ctg ggc tcc   1186
Gln Ala Phe Glu Tyr Gly Ile Lys Lys Gly Arg Gln Gly Leu Gly Ser
325                 330                 335 att ttc gtc tgg gca tct ggg aat ggc ggg aga gag ggg gac tac tgc   1234
Ile Phe Val Trp Ala Ser Gly Asn Gly Gly Arg Glu Gly Asp Tyr Cys
340                 345                 350                 355 tcg tgc gat ggc tac acc aac agc atc tac acc atc tcc gtc agc agc   1282
Ser Cys Asp Gly Tyr Thr Asn Ser Ile Tyr Thr Ile Ser Val Ser Ser
                360                 365                 370 gcc acc gag aat ggc tac aag ccc tgg tac ctg gaa gag tgt gcc tcc   1330
Ala Thr Glu Asn Gly Tyr Lys Pro Trp Tyr Leu Glu Glu Cys Ala Ser
                375                 380                 385 acc ctg gcc acc acc tac agc agt ggg gcc ttt tat gag cga aaa atc   1378
Thr Leu Ala Thr Thr Tyr Ser Ser Gly Ala Phe Tyr Glu Arg Lys Ile
            390                 395                 400 gtc acc acg gat ctg cgt cag cgc tgt acc gat ggc cac act ggg acc   1426
Val Thr Thr Asp Leu Arg Gln Arg Cys Thr Asp Gly His Thr Gly Thr
        405                 410                 415 tca gtc tct gcc ccc atg gtg gcg ggc atc atc gcc ttg gct cta gaa   1474
Ser Val Ser Ala Pro Met Val Ala Gly Ile Ile Ala Leu Ala Leu Glu
420                 425                 430                 435 gca aac agc cag tta acc tgg agg gac gtc cag cac ctg cta gtg aag   1522
Ala Asn Ser Gln Leu Thr Trp Arg Asp Val Gln His Leu Leu Val Lys
                440                 445                 450 aca tcc cgg ccg gcc cac ctg aaa gcg agc gac tgg aaa gta aac ggc   1570
Thr Ser Arg Pro Ala His Leu Lys Ala Ser Asp Trp Lys Val Asn Gly
                455                 460                 465 gcg ggt cat aaa gtt agc cat ttc tat gga ttt ggt ttg gtg gac gca   1618
Ala Gly His Lys Val Ser His Phe Tyr Gly Phe Gly Leu Val Asp Ala
            470                 475                 480 gaa gct ctc gtt gtg gag gca aag aag tgg aca gca gtg cca tcg cag   1666
Glu Ala Leu Val Val Glu Ala Lys Lys Trp Thr Ala Val Pro Ser Gln
485                 490                 495 cac atg tgt gtg gcc gcc tcg gac aag aga ccc agg agc atc ccc tta   1714
His Met Cys Val Ala Ala Ser Asp Lys Arg Pro Arg Ser Ile Pro Leu
500                 505                 510                 515 gtg cag gtg ctg cgg act acg gcc ctg acc agc gcc tgc gcg gag cac   1762
Val Gln Val Leu Arg Thr Thr Ala Leu Thr Ser Ala Cys Ala Glu His
                520                 525                 530 tcg gac cag cgg gtg gtc tac ttg gag cac gtg gtg ttc gcc acc tcc   1810
Ser Asp Gln Arg Val Val Tyr Leu Glu His Val Val Phe Arg Thr Ser
            535                 540                 545
```

-continued

```
atc tca cac cca cgc cga gga gac ctc cag atc tac ctg gtt tct ccc      1858
Ile Ser His Pro Arg Arg Gly Asp Leu Gln Ile Tyr Leu Val Ser Pro
        550                 555                 560 tcg gga acc aag tct caa ctt ttg gca aag agg ttg ctg gat ctt tcc      1906
Ser Gly Thr Lys Ser Gln Leu Leu Ala Lys Arg Leu Leu Asp Leu Ser
    565                 570                 575 aat gaa ggg ttt aca aac tgg gaa ttc atg act gtc cac tgc tgg gga      1954
Asn Glu Gly Phe Thr Asn Trp Glu Phe Met Thr Val His Cys Trp Gly
580                 585                 590                 595 gaa aag gct gaa ggg cag tgg acc ttg gaa atc caa gat ctg cca tcc      2002
Glu Lys Ala Glu Gly Gln Trp Thr Leu Glu Ile Gln Asp Leu Pro Ser
                600                 605                 610 cag gtc cgc aac ccg gag aag caa ggg aag ttg aaa gaa tgg agc ctc      2050
Gln Val Arg Asn Pro Glu Lys Gln Gly Lys Leu Lys Glu Trp Ser Leu
            615                 620                 625 ata ctg tat ggc aca gca gag cac ccg tac cac acc ttc agt gcc cat      2098
Ile Leu Tyr Gly Thr Ala Glu His Pro Tyr His Thr Phe Ser Ala His
        630                 635                 640 cag tcc cgc tcg cgg atg ctg gag ctc tca gcc cca gag ctg gag cca      2146
Gln Ser Arg Ser Arg Met Leu Glu Leu Ser Ala Pro Glu Leu Glu Pro
    645                 650                 655 ccc aag gct gcc ctg tca ccc tcc cag gtg gaa gtt cct gaa gat gag      2194
Pro Lys Ala Ala Leu Ser Pro Ser Gln Val Glu Val Pro Glu Asp Glu
660                 665                 670                 675 gaa gat tac aca gct caa tcc acc cca ggc tct gct aat att tta cag      2242
Glu Asp Tyr Thr Ala Gln Ser Thr Pro Gly Ser Ala Asn Ile Leu Gln
                680                 685                 690 acc agt gtg tgc cat ccg gag tgt ggt gac aaa ggc tgt gat ggc ccc      2290
Thr Ser Val Cys His Pro Glu Cys Gly Asp Lys Gly Cys Asp Gly Pro
            695                 700                 705 aat gca gac cag tgc ttg aac tgc gtc cac ttc agc ctg ggg agt gtc      2338
Asn Ala Asp Gln Cys Leu Asn Cys Val His Phe Ser Leu Gly Ser Val
        710                 715                 720 aag acc agc agg aag tgc gtg agt gtg tgc ccc ttg ggc tac ttt ggg      2386
Lys Thr Ser Arg Lys Cys Val Ser Val Cys Pro Leu Gly Tyr Phe Gly
    725                 730                 735 gac aca gca gca aga cgc tgt cgc cgg tgc cac aag ggg tgt gag acc      2434
Asp Thr Ala Ala Arg Arg Cys Arg Arg Cys His Lys Gly Cys Glu Thr
740                 745                 750                 755 tgc tcc agc aga gct gcg acg cag tgc ctg tct tgc cgc cgc ggg ttc      2482
Cys Ser Ser Arg Ala Ala Thr Gln Cys Leu Ser Cys Arg Arg Gly Phe
                760                 765                 770 tat cac cac cag gag atg aac acc tgt gtg acc ctc tgt cct gca gga      2530
Tyr His His Gln Glu Met Asn Thr Cys Val Thr Leu Cys Pro Ala Gly
            775                 780                 785 ttt tat gct gat gaa agt cag aaa aat tgc ctt aaa tgc cac cca agc      2578
Phe Tyr Ala Asp Glu Ser Gln Lys Asn Cys Leu Lys Cys His Pro Ser
        790                 795                 800 tgt aaa aag tgc gtg gat gaa cct gag aaa tgt act gtc tgt aaa gaa      2626
Cys Lys Lys Cys Val Asp Glu Pro Glu Lys Cys Thr Val Cys Lys Glu
    805                 810                 815 gga ttc agc ctt gca cgg ggc agc tgc att cct gac tgt gag cca ggc      2674
Gly Phe Ser Leu Ala Arg Gly Ser Cys Ile Pro Asp Cys Glu Pro Gly
820                 825                 830                 835 acc tac ttt gac tca gag ctg atc aga tgt ggg gaa tgc cat cac acc      2722
Thr Tyr Phe Asp Ser Glu Leu Ile Arg Cys Gly Glu Cys His His Thr
                840                 845                 850 tgc gga acc tgc gtg ggg cca ggc aga gaa gag tgc att cac tgt gcg      2770
Cys Gly Thr Cys Val Gly Pro Gly Arg Glu Glu Cys Ile His Cys Ala
```

```
                855                 860                 865
aaa aac ttc cac ttc cac gac tgg aag tgt gtg cca gcc tgt ggt gag      2818
Lys Asn Phe His Phe His Asp Trp Lys Cys Val Pro Ala Cys Gly Glu
            870                 875                 880 ggc ttc tac cca gaa gag atg ccg ggc ttg ccc cac aaa gtg tgt cga      2866
Gly Phe Tyr Pro Glu Glu Met Pro Gly Leu Pro His Lys Val Cys Arg
        885                 890                 895 agg tgt gac gag aac tgc ttg agc tgt gca ggc tcc agc agg aac tgt      2914
Arg Cys Asp Glu Asn Cys Leu Ser Cys Ala Gly Ser Ser Arg Asn Cys
900                 905                 910                 915 agc agg tgt aag acg ggc ttc aca cag ctg ggg acc tcc tgc atc acc      2962
Ser Arg Cys Lys Thr Gly Phe Thr Gln Leu Gly Thr Ser Cys Ile Thr
                920                 925                 930 aac cac acg tgc agc aac gct gac gag aca ttc tgc gag atg gtg aag      3010
Asn His Thr Cys Ser Asn Ala Asp Glu Thr Phe Cys Glu Met Val Lys
            935                 940                 945 tcc aac cgg ctg tgc gaa cgg aag ctc ttc att cag ttc tgc tgc cgc      3058
Ser Asn Arg Leu Cys Glu Arg Lys Leu Phe Ile Gln Phe Cys Cys Arg
        950                 955                 960 acg tgc ctc ctg gcc ggg taagggtgcc tagctgccca cagagggcag              3106
Thr Cys Leu Leu Ala Gly
        965 gcactcccat ccatccatcc gtccaccttc ctccagactg tcggccagag tctgtttcag    3166 gagcggcgcc ctgcacctga cagctttatc tccccaggag cagcatctct gagcacccaa    3226 gccaggtggg tggtggctct taaggagtg ttcctaaaat ggtgatatcc tctcaaatgc     3286 tgcttgttgg ctccagtctt ccgacaaact aacaggaaca aaatgaattc tgggaatcca    3346 cagctctggc tttggagcag cttctgggac cataagttta ctgaatcttc aagaccaaag    3406 cagaaaagaa aggcgcttgg catcacacat cactcttctc cccgtgcttt tctgcggctg    3466 tgtagtaaat ctccccggcc cagctggcga accctgggcc atcctcacat gtgacaaagg    3526 gccagcagtc tacctgctcg ttgcctgcca ctgagcagtc tggggacggt ttggtcagac    3586 tataaataag ataggtttga gggcataaaa tgtatgacca ctggggccgg agtatctatt    3646 tctacatagt cagctacttc tgaaactgca gcagtggctt agaaagtcca attccaaagc    3706 cagaccagaa gattctatcc cccgcagcgc tctcctttga gcaagccgag ctctccttgt    3766 taccgtgttc tgtctgtgtc ttcaggagtc tcatggcctg aacgaccacc tcgacctgat    3826 gcagagcctt ctgaggagag caacaggag cattctgtg gccagccaaa aggtaccccg      3886 atggccaagc aattcctctg aacaaaatgt aaagccagcc atgcattgtt aatcatccat    3946 cacttcccat tttatggaat tgcttttaaa atacatttgg cctctgccct tcagaagact    4006 cgttttaag gtggaaactc ctgtgtctgt gtatattaca agcctacatg acacagttgg     4066 atttattctg ccaaacctgt gtaggcattt tataagctac atgttctaat ttttaccgat    4126 gttaattatt ttgacaaata tttcatatat tttcattgaa atgcacagat ctgcttgatc    4186 aattcccttg aatagggaag taacatttgc cttaaatttt ttcgacctcg tctttctcca    4246 tattgtcctg ctcccctgtt tgacgacagt gcatttgcct tgtcacctgt gagctggaga    4306 gaacccagat gttgtttatt gaatctacaa ctctgaaaga gaaatcaatg aagcaagtac    4366 aatgttaacc ctaaattaat aaaagagtta acatccc                             4403
```

<210> SEQ ID NO 2
<211> LENGTH: 969
<212> TYPE: PRT
<213> ORGANISM: Homo sapiens

<400> SEQUENCE: 2

```
Met Pro Pro Arg Ala Pro Ala Pro Gly Pro Arg Pro Pro Arg
  1               5                  10                  15

Ala Ala Ala Ala Thr Asp Thr Ala Ala Gly Ala Gly Gly Ala Gly Gly
                 20                  25                  30

Ala Gly Gly Ala Gly Gly Pro Gly Phe Arg Pro Leu Ala Pro Arg Pro
             35                  40                  45

Trp Arg Trp Leu Leu Leu Leu Ala Leu Pro Ala Ala Cys Ser Ala Pro
         50                  55                  60

Pro Pro Arg Pro Val Tyr Thr Asn His Trp Ala Val Gln Val Leu Gly
 65                  70                  75                  80

Gly Pro Ala Glu Ala Asp Arg Val Ala Ala Ala His Gly Tyr Leu Asn
                 85                  90                  95

Leu Gly Gln Ile Gly Asn Leu Glu Asp Tyr Tyr His Phe Tyr His Ser
                100                 105                 110

Lys Thr Phe Lys Arg Ser Thr Leu Ser Ser Arg Gly Pro His Thr Phe
            115                 120                 125

Leu Arg Met Asp Pro Gln Val Lys Trp Leu Gln Gln Gln Glu Val Lys
        130                 135                 140

Arg Arg Val Lys Arg Gln Val Arg Ser Asp Pro Gln Ala Leu Tyr Phe
145                 150                 155                 160

Asn Asp Pro Ile Trp Ser Asn Met Trp Tyr Leu His Cys Gly Asp Lys
                165                 170                 175

Asn Ser Arg Cys Arg Ser Glu Met Asn Val Gln Ala Ala Trp Lys Arg
            180                 185                 190

Gly Tyr Thr Gly Lys Asn Val Val Val Thr Ile Leu Asp Asp Gly Ile
        195                 200                 205

Glu Arg Asn His Pro Asp Leu Ala Pro Asn Tyr Asp Ser Tyr Ala Ser
210                 215                 220

Tyr Asp Val Asn Gly Asn Asp Tyr Asp Pro Ser Pro Arg Tyr Asp Ala
225                 230                 235                 240

Ser Asn Glu Asn Lys His Gly Thr Arg Cys Ala Gly Glu Val Ala Ala
                245                 250                 255

Ser Ala Asn Asn Ser Tyr Cys Ile Val Gly Ile Ala Tyr Asn Ala Lys
            260                 265                 270

Ile Gly Gly Ile Arg Met Leu Asp Gly Asp Val Thr Asp Val Val Glu
        275                 280                 285

Ala Lys Ser Leu Gly Ile Arg Pro Asn Tyr Ile Asp Ile Tyr Ser Ala
290                 295                 300

Ser Trp Gly Pro Asp Asp Gly Lys Thr Val Asp Gly Pro Gly Arg
305                 310                 315                 320

Leu Ala Lys Gln Ala Phe Glu Tyr Gly Ile Lys Lys Gly Arg Gln Gly
            325                 330                 335

Leu Gly Ser Ile Phe Val Trp Ala Ser Gly Asn Gly Gly Arg Glu Gly
        340                 345                 350

Asp Tyr Cys Ser Cys Asp Gly Tyr Thr Asn Ser Ile Tyr Thr Ile Ser
        355                 360                 365

Val Ser Ser Ala Thr Glu Asn Gly Tyr Lys Pro Trp Tyr Leu Glu Glu
        370                 375                 380

Cys Ala Ser Thr Leu Ala Thr Thr Tyr Ser Ser Gly Ala Phe Tyr Glu
385                 390                 395                 400

Arg Lys Ile Val Thr Thr Asp Leu Arg Gln Arg Cys Thr Asp Gly His
```

```
                         405                 410                 415
Thr Gly Thr Ser Val Ser Ala Pro Met Val Ala Gly Ile Ile Ala Leu
            420                 425                 430
Ala Leu Glu Ala Asn Ser Gln Leu Thr Trp Arg Asp Val Gln His Leu
            435                 440                 445
Leu Val Lys Thr Ser Arg Pro Ala His Leu Lys Ala Ser Asp Trp Lys
450                 455                 460
Val Asn Gly Ala Gly His Lys Val Ser His Phe Tyr Gly Phe Gly Leu
465                 470                 475                 480
Val Asp Ala Glu Ala Leu Val Val Glu Ala Lys Lys Trp Thr Ala Val
                485                 490                 495
Pro Ser Gln His Met Cys Val Ala Ala Ser Asp Lys Arg Pro Arg Ser
            500                 505                 510
Ile Pro Leu Val Gln Val Leu Arg Thr Thr Ala Leu Thr Ser Ala Cys
            515                 520                 525
Ala Glu His Ser Asp Gln Arg Val Val Tyr Leu Glu His Val Val Val
            530                 535                 540
Arg Thr Ser Ile Ser His Pro Arg Arg Gly Asp Leu Gln Ile Tyr Leu
545                 550                 555                 560
Val Ser Pro Ser Gly Thr Lys Ser Gln Leu Leu Ala Lys Arg Leu Leu
                565                 570                 575
Asp Leu Ser Asn Glu Gly Phe Thr Asn Trp Glu Phe Met Thr Val His
            580                 585                 590
Cys Trp Gly Glu Lys Ala Glu Gly Gln Trp Thr Leu Glu Ile Gln Asp
            595                 600                 605
Leu Pro Ser Gln Val Arg Asn Pro Glu Lys Gln Gly Lys Leu Lys Glu
610                 615                 620
Trp Ser Leu Ile Leu Tyr Gly Thr Ala Glu His Pro Tyr His Thr Phe
625                 630                 635                 640
Ser Ala His Gln Ser Arg Ser Arg Met Leu Glu Leu Ser Ala Pro Glu
                645                 650                 655
Leu Glu Pro Pro Lys Ala Ala Leu Ser Pro Gln Val Glu Val Pro
            660                 665                 670
Glu Asp Glu Glu Asp Tyr Thr Ala Gln Ser Thr Pro Gly Ser Ala Asn
            675                 680                 685
Ile Leu Gln Thr Ser Val Cys His Pro Glu Cys Gly Asp Lys Gly Cys
            690                 695                 700
Asp Gly Pro Asn Ala Asp Gln Cys Leu Asn Cys Val His Phe Ser Leu
705                 710                 715                 720
Gly Ser Val Lys Thr Ser Arg Lys Cys Val Ser Val Cys Pro Leu Gly
                725                 730                 735
Tyr Phe Gly Asp Thr Ala Ala Arg Arg Cys Arg Arg Cys His Lys Gly
            740                 745                 750
Cys Glu Thr Cys Ser Ser Arg Ala Ala Thr Gln Cys Leu Ser Cys Arg
            755                 760                 765
Arg Gly Phe Tyr His His Gln Glu Met Asn Thr Cys Val Thr Leu Cys
            770                 775                 780
Pro Ala Gly Phe Tyr Ala Asp Glu Ser Gln Lys Asn Cys Leu Lys Cys
785                 790                 795                 800
His Pro Ser Cys Lys Lys Cys Val Asp Glu Pro Glu Lys Cys Thr Val
                805                 810                 815
Cys Lys Glu Gly Phe Ser Leu Ala Arg Gly Ser Cys Ile Pro Asp Cys
            820                 825                 830
```

```
Glu Pro Gly Thr Tyr Phe Asp Ser Glu Leu Ile Arg Cys Gly Glu Cys
        835                 840                 845

His His Thr Cys Gly Thr Cys Val Gly Pro Gly Arg Glu Glu Cys Ile
865                 855                 860

His Cys Ala Lys Asn Phe His Phe His Asp Trp Lys Cys Val Pro Ala
865                 870                 875                 880

Cys Gly Glu Gly Phe Tyr Pro Glu Glu Met Pro Gly Leu Pro His Lys
                    885                 890                 895

Val Cys Arg Arg Cys Asp Glu Asn Cys Leu Ser Cys Ala Gly Ser Ser
            900                 905                 910

Arg Asn Cys Ser Arg Cys Lys Thr Gly Phe Thr Gln Leu Gly Thr Ser
        915                 920                 925

Cys Ile Thr Asn His Thr Cys Ser Asn Ala Asp Glu Thr Phe Cys Glu
        930                 935                 940

Met Val Lys Ser Asn Arg Leu Cys Glu Arg Lys Leu Phe Ile Gln Phe
945                 950                 955                 960

Cys Cys Arg Thr Cys Leu Leu Ala Gly
                965
```

```
<210> SEQ ID NO 3
<211> LENGTH: 636
<212> TYPE: DNA
<213> ORGANISM: Homo sapiens
<220> FEATURE:
<221> NAME/KEY: CDS
<222> LOCATION: (1)..(57)

<400> SEQUENCE: 3 ggt cat aaa ggt gcg gca gtg gcg ttc tgg tgg acc att ggg tgg ccc     48
Gly His Lys Gly Ala Ala Val Ala Phe Trp Trp Thr Ile Gly Trp Pro
  1               5                  10                  15 tgg aat gtg taggaagggg tgtcatgaat tccttaaaag gactctccaa             97
Trp Asn Val atagcattag ttgttattat taacttaaaa ggactctcca aatagcatta gttgttatta   157
ttaattgtgt gtcacaagaa tttaaaacgc atgtgcagct atttaagaaa agtatcccgg   217
aagctcacag tgacattacg gaagaaccct caggtcacaa gagtctgggg tctcctatac   277
tctataactt tggccacacc gagacaccac ctataccaat atttactcat agttctcttt   337
aagccaggag caatgacgtg tgcctatagt cgcagctact agggaagttg aggcaggagg   397
attgcttgag cccaggaatt tgagtctagc ctggacaaca cagcaggact ccatctctta   457
aaaaaaaaat tacttccccc actactttt ttgacataaa aaatgtatt ttaaaaggaa     517 actgtactac atctagttaa tcataggttt gatatgtagt tacgtatttt ttctaatgtg   577
cattaaaaca aatccataat tattaaaata aatgttgttt gtgtgccaaa aaaaaaaa     636

<210> SEQ ID NO 4
<211> LENGTH: 19
<212> TYPE: PRT
<213> ORGANISM: Homo sapiens

<400> SEQUENCE: 4

Gly His Lys Gly Ala Ala Val Ala Phe Trp Trp Thr Ile Gly Trp Pro
  1               5                  10                  15

Trp Asn Val

<210> SEQ ID NO 5
```

```
<211> LENGTH: 148
<212> TYPE: DNA
<213> ORGANISM: Homo sapiens
<220> FEATURE:
<221> NAME/KEY: CDS
<222> LOCATION: (18)..(131)

<400> SEQUENCE: 5
ggcctgtctt ttcagtt agc cat ttc tat gga ttt ggt ttg gtg gac gca      50
                   Ser His Phe Tyr Gly Phe Gly Leu Val Asp Ala
                    1               5                  10 gaa gct ctc gtt gtg gag gca aag aag tgg aca gca gtg cca tcg cag      98
Glu Ala Leu Val Val Glu Ala Lys Lys Trp Thr Ala Val Pro Ser Gln
            15                  20                  25 cac atg tgt gtg gcc gcc tcg gac aag aga ccc aggtaaggct ctgctgt      148
His Met Cys Val Ala Ala Ser Asp Lys Arg Pro
         30                  35

<210> SEQ ID NO 6
<211> LENGTH: 38
<212> TYPE: PRT
<213> ORGANISM: Homo sapiens

<400> SEQUENCE: 6

Ser His Phe Tyr Gly Phe Gly Leu Val Asp Ala Glu Ala Leu Val Val
 1               5                  10                  15

Glu Ala Lys Lys Trp Thr Ala Val Pro Ser Gln His Met Cys Val Ala
            20                  25                  30

Ala Ser Asp Lys Arg Pro
            35

<210> SEQ ID NO 7
<211> LENGTH: 280
<212> TYPE: PRT
<213> ORGANISM: Saccharomyces cerevisiae

<400> SEQUENCE: 7

Asn Asp Pro Leu Phe Glu Arg Gln Trp His Leu Val Asn Pro Ser Phe
 1               5                  10                  15

Pro Gly Ser Asp Ile Asn Val Leu Asp Leu Trp Tyr Asn Asn Ile Thr
            20                  25                  30

Gly Ala Gly Val Val Ala Ala Ile Val Asp Asp Gly Leu Asp Tyr Glu
        35                  40                  45

Asn Glu Asp Leu Lys Asp Asn Phe Cys Ala Glu Gly Ser Trp Asp Phe
    50                  55                  60

Asn Asp Asn Thr Asn Leu Pro Lys Pro Arg Leu Ser Asp Asp Tyr His
65                  70                  75                  80

Gly Thr Arg Cys Ala Gly Glu Ile Ala Ala Lys Lys Gly Asn Asn Phe
                85                  90                  95

Cys Gly Val Gly Val Gly Tyr Asn Ala Lys Ile Ser Gly Ile Arg Ile
            100                 105                 110

Leu Ser Gly Asp Ile Thr Thr Glu Asp Glu Ala Ala Ser Leu Ile Tyr
        115                 120                 125

Gly Leu Asp Val Asn Asp Ile Tyr Ser Cys Ser Trp Gly Pro Ala Asp
    130                 135                 140

Asp Gly Arg His Leu Gln Gly Pro Ser Asp Leu Val Lys Lys Ala Leu
145                 150                 155                 160

Val Lys Gly Val Thr Glu Gly Arg Asp Ser Lys Gly Ala Ile Tyr Val
                165                 170                 175
```

```
Phe Ala Ser Gly Asn Gly Gly Thr Arg Gly Asp Asn Cys Asn Tyr Asp
            180                 185                 190

Gly Tyr Thr Asn Ser Ile Tyr Ser Ile Thr Ile Gly Ala Ile Asp His
            195                 200                 205

Lys Asp Leu His Pro Pro Tyr Ser Glu Gly Cys Ser Ala Val Met Ala
210                 215                 220

Val Thr Tyr Ser Ser Gly Ser Gly Glu Tyr Ile His Ser Ser Asp Ile
225                 230                 235                 240

Asn Gly Arg Cys Ser Asn Ser His Gly Gly Thr Ser Ala Ala Ala Pro
                245                 250                 255

Leu Ala Ala Gly Val Tyr Thr Leu Leu Leu Glu Ala Asn Pro Asn Leu
                260                 265                 270

Thr Trp Arg Asp Val Gln Tyr Leu
            275                 280

<210> SEQ ID NO 8
<211> LENGTH: 282
<212> TYPE: PRT
<213> ORGANISM: Homo sapiens

<400> SEQUENCE: 8

Asp Pro Lys Phe Pro Gln Gln Trp Tyr Leu Ser Gly Val Thr Gln Arg
1               5                   10                  15

Asp Leu Asn Val Lys Ala Ala Trp Ala Gln Gly Tyr Thr Gly His Gly
            20                  25                  30

Ile Val Val Ser Ile Leu Asp Asp Gly Ile Glu Lys Asn His Pro Asp
            35                  40                  45

Leu Ala Gly Asn Tyr Asp Pro Gly Ala Ser Phe Asp Val Asn Asp Gln
        50                  55                  60

Asp Pro Asp Pro Gln Pro Arg Tyr Thr Gln Met Asn Asp Asn Arg His
65                  70                  75                  80

Gly Thr Arg Cys Ala Gly Glu Val Ala Val Ala Asn Asn Gly Val
                85                  90                  95

Cys Gly Val Gly Val Ala Tyr Asn Ala Arg Ile Gly Gly Val Arg Met
                100                 105                 110

Leu Asp Gly Glu Val Thr Asp Ala Val Glu Ala Arg Ser Leu Gly Leu
            115                 120                 125

Asn Pro Asn His Ile His Ile Tyr Ser Ala Ser Trp Gly Pro Glu Asp
130                 135                 140

Asp Gly Lys Thr Val Asp Gly Pro Ala Arg Leu Ala Glu Glu Ala Phe
145                 150                 155                 160

Phe Arg Gly Val Ser Gln Gly Arg Gly Gly Leu Gly Ser Ile Phe Val
                165                 170                 175

Trp Ala Ser Gly Asn Gly Gly Arg Glu His Asp Ser Cys Asn Cys Asp
            180                 185                 190

Gly Tyr Thr Asn Ser Ile Tyr Thr Leu Ser Ile Ser Ser Ala Thr Gln
            195                 200                 205

Phe Gly Asn Val Pro Trp Tyr Ser Glu Ala Cys Ser Ser Thr Leu Ala
        210                 215                 220

Thr Thr Tyr Ser Ser Gly Asn Gln Asn Glu Lys Gln Ile Val Thr Thr
225                 230                 235                 240

Asp Leu Arg Gln Lys Cys Thr Glu Ser His Thr Gly Thr Ser Ala Ser
                245                 250                 255

Ala Pro Leu Ala Ala Gly Ile Ile Ala Leu Thr Leu Glu Ala Asn Lys
        260                 265                 270
```

```
Asn Leu Thr Trp Arg Asp Met Gln His Leu
        275                 280
```

```
<210> SEQ ID NO 9
<211> LENGTH: 291
<212> TYPE: PRT
<213> ORGANISM: Homo sapiens

<400> SEQUENCE: 9
```

```
Asn Asp Pro Leu Phe Thr Lys Gln Trp Tyr Leu Ile Asn Thr Gly Gln
 1               5                  10                  15

Ala Asp Gly Thr Pro Gly Leu Asp Leu Asn Val Ala Glu Ala Trp Glu
            20                  25                  30

Leu Gly Tyr Thr Gly Lys Gly Val Thr Ile Gly Ile Met Asp Asp Gly
        35                  40                  45

Ile Asp Tyr Leu His Pro Asp Leu Ala Ser Asn Tyr Asn Ala Glu Ala
    50                  55                  60

Ser Tyr Asp Phe Ser Ser Asn Asp Pro Tyr Pro Tyr Pro Arg Tyr Thr
65                  70                  75                  80

Asp Asp Trp Phe Asn Ser His Gly Thr Arg Cys Ala Gly Glu Val Ser
                85                  90                  95

Ala Ala Ala Asn Asn Ile Cys Gly Val Gly Val Ala Tyr Asn Ser
            100                 105                 110

Lys Val Ala Gly Ile Arg Met Leu Asp Gln Pro Phe Met Thr Asp Ile
        115                 120                 125

Ile Glu Ala Ser Ser Ile Ser His Met Pro Gln Leu Ile Asp Ile Tyr
    130                 135                 140

Ser Ala Ser Trp Gly Pro Thr Asp Asn Gly Lys Thr Val Asp Gly Pro
145                 150                 155                 160

Arg Asp Val Thr Leu Gln Ala Met Ala Asp Gly Val Asn Lys Gly Arg
                165                 170                 175

Gly Gly Lys Gly Ser Ile Tyr Val Trp Ala Ser Gly Asp Gly Gly Ser
            180                 185                 190

Tyr Asp Asp Cys Asn Cys Asp Gly Tyr Ala Ser Ser Met Trp Thr Ile
        195                 200                 205

Ser Ile Asn Ser Ala Ile Asn Asp Gly Arg Thr Ala Leu Tyr Asp Glu
    210                 215                 220

Ser Cys Ser Ser Thr Leu Ala Ser Thr Phe Ser Asn Gly Arg Lys Arg
225                 230                 235                 240

Asn Pro Glu Ala Gly Val Ala Thr Thr Asp Leu Tyr Gly Asn Cys Thr
                245                 250                 255

Leu Arg His Ser Gly Thr Ser Ala Ala Ala Pro Glu Ala Ala Gly Val
            260                 265                 270

Phe Ala Leu Ala Leu Glu Ala Asn Leu Gly Leu Thr Trp Arg Asp Met
        275                 280                 285

Gln His Leu
    290
```

```
<210> SEQ ID NO 10
<211> LENGTH: 289
<212> TYPE: PRT
<213> ORGANISM: Mus musculus

<400> SEQUENCE: 10
```

```
Asn Asp Pro Met Trp Asn Gln Gln Trp Tyr Leu Gln Asp Thr Arg Met
 1               5                  10                  15
```

Thr Ala Ala Leu Pro Lys Leu Asp Leu His Val Ile Pro Val Trp Glu
            20                  25                  30

Lys Gly Ile Thr Gly Lys Gly Val Val Ile Thr Val Leu Asp Asp Gly
                35                  40                  45

Leu Glu Trp Asn His Thr Asp Ile Tyr Ala Asn Tyr Asp Pro Glu Ala
            50                  55                  60

Ser Tyr Asp Phe Asn Asp Asn Asp His Asp Pro Phe Pro Arg Tyr Asp
 65                 70                  75                  80

Leu Thr Asn Glu Asn Lys His Gly Thr Arg Cys Ala Gly Glu Ile Ala
                85                  90                  95

Met Gln Ala Asn Asn His Lys Cys Gly Val Gly Val Ala Tyr Asn Ser
            100                 105                 110

Lys Val Gly Gly Ile Arg Met Leu Asp Gly Ile Val Thr Asp Ala Ile
            115                 120                 125

Glu Ala Ser Ser Ile Gly Phe Asn Pro Gly His Val Asp Ile Tyr Ser
            130                 135                 140

Ala Ser Trp Gly Pro Asn Asp Asp Gly Lys Thr Val Glu Gly Pro Gly
145                 150                 155                 160

Arg Leu Ala Gln Lys Ala Phe Glu Tyr Gly Val Lys Gln Gly Arg Gln
                165                 170                 175

Gly Lys Gly Ser Ile Phe Val Trp Ala Ser Gly Asn Gly Gly Arg Gln
            180                 185                 190

Gly Asp Asn Cys Asp Cys Asp Gly Tyr Thr Asp Ser Ile Tyr Thr Ile
            195                 200                 205

Ser Ile Ser Ser Ala Ser Gln Gln Gly Leu Ser Pro Trp Tyr Ala Glu
            210                 215                 220

Lys Cys Ser Ser Thr Leu Ala Thr Ser Tyr Ser Ser Gly Asp Tyr Thr
225                 230                 235                 240

Asp Gln Arg Ile Thr Ser Ala Asp Leu His Asn Asp Cys Thr Glu Thr
                245                 250                 255

His Thr Gly Thr Ser Ala Ser Ala Pro Leu Ala Ala Gly Ile Phe Ala
            260                 265                 270

Leu Ala Leu Glu Ala Asn Pro Asn Leu Thr Trp Arg Asp Met Gln His
            275                 280                 285

Leu

<210> SEQ ID NO 11
<211> LENGTH: 287
<212> TYPE: PRT
<213> ORGANISM: Homo sapiens

<400> SEQUENCE: 11

Asn Asp Pro Ile Trp Ser Asn Met Trp Tyr Leu His Cys Gly Asp Lys
 1               5                  10                  15

Asn Ser Arg Cys Arg Ser Glu Met Asn Val Gln Ala Ala Trp Lys Arg
                20                  25                  30

Gly Tyr Thr Gly Lys Asn Val Val Val Thr Ile Leu Asp Asp Gly Ile
            35                  40                  45

Glu Arg Asn His Pro Asp Leu Ala Pro Asn Tyr Asp Ser Tyr Ala Ser
         50                    55                  60

Tyr Asp Val Asn Gly Asn Asp Tyr Asp Pro Ser Pro Arg Tyr Asp Ala
 65                 70                  75                  80

Ser Asn Glu Asn Lys His Gly Thr Arg Cys Ala Gly Glu Val Ala Ala
                85                  90                  95

```
Ser Ala Asn Asn Ser Tyr Cys Ile Val Gly Ile Ala Tyr Asn Ala Lys
                100                 105                 110

Ile Gly Gly Ile Arg Met Leu Asp Gly Asp Val Thr Asp Val Val Glu
            115                 120                 125

Ala Lys Ser Leu Gly Ile Arg Pro Asn Tyr Ile Asp Ile Tyr Ser Ala
        130                 135                 140

Ser Trp Gly Pro Asp Asp Gly Lys Thr Val Asp Gly Pro Gly Arg
145                 150                 155                 160

Leu Ala Lys Gln Ala Phe Glu Tyr Gly Ile Lys Lys Gly Arg Gln Gly
                165                 170                 175

Leu Gly Ser Ile Phe Val Trp Ala Ser Gly Asn Gly Gly Arg Glu Gly
            180                 185                 190

Asp Tyr Cys Ser Cys Asp Gly Tyr Thr Asn Ser Ile Tyr Thr Ile Ser
        195                 200                 205

Val Ser Ser Ala Thr Glu Asn Gly Tyr Lys Pro Trp Tyr Leu Glu Glu
    210                 215                 220

Cys Ala Ser Thr Leu Ala Thr Thr Tyr Ser Ser Gly Ala Phe Tyr Glu
225                 230                 235                 240

Arg Lys Ile Val Thr Thr Asp Leu Arg Gln Arg Cys Thr Asp Gly His
                245                 250                 255

Thr Gly Thr Ser Val Ser Ala Pro Met Val Ala Gly Ile Ile Leu Ala
            260                 265                 270

Leu Glu Ala Asn Ser Gln Leu Thr Trp Arg Asp Val Gln His Leu
        275                 280                 285

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:SYNTHETIC
      DNA PCR PRIMER
<220> FEATURE:
<221> NAME/KEY: misc_difference
<222> LOCATION: (15)
<223> OTHER INFORMATION: T or C
<220> FEATURE:
<221> NAME/KEY: misc_difference
<222> LOCATION: (18)
<223> OTHER INFORMATION: T or C
<220> FEATURE:
<221> NAME/KEY: misc_difference
<222> LOCATION: (21)
<223> OTHER INFORMATION: A, C, G, or T

<400> SEQUENCE: 12
agatctgaat tcgaygaygg nat                                         23

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:SYNTHETIC
      DNA PCR PRIMER
<220> FEATURE:
<221> NAME/KEY: misc_difference
<222> LOCATION: (18)
<223> OTHER INFORMATION: G or T
<220> FEATURE:
<221> NAME/KEY: misc_difference
<222> LOCATION: (19)
<223> OTHER INFORMATION: A, C, G or T
<220> FEATURE:
```

-continued

```
<221> NAME/KEY: misc_difference
<222> LOCATION: (22)
<223> OTHER INFORMATION: A, C, G or T
<220> FEATURE:
<221> NAME/KEY: misc_difference
<222> LOCATION: (25)
<223> OTHER INFORMATION: A or G

<400> SEQUENCE: 13
agatctaagc ttacacckng tnccrtg                                          27

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:SYNTHETIC
      DNA PCR PRIMER

<400> SEQUENCE: 14
tattcattgc cgttcacgtc gtag                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:SYNTHETIC
      DNA PCR PRIMER

<400> SEQUENCE: 15
tattcattgc cgttcacgtc gtag                                             24

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:SYNTHETIC
      DNA PCR PRIMER

<400> SEQUENCE: 16
ggaggcatag cggcgac                                                     17
```

COMPOSITIONS AND METHODS FOR PACE 4 AND 4.1 GENE AND POLYPEPTIDES IN CELLS

CROSS REFERENCE TO RELATED APPLICATIONS

This application is a continuation of application Ser. No. 08/447,642, filed May 23, 1995 now U.S. Pat. No. 5,989,890, which is a divisional of application Ser. No. 08/284,941, filed August 2, 1994 now U.S. Pat. No. 5,863,756, which is a continuation of application Ser. No. 07/848,629, filed Mar. 9, 1992, now abandoned.

BACKGROUND OF THE INVENTION

1. Field of the Disclosure

This invention relates generally to proteins and their production in recombinant host cells. More particularly, it relates to polynucleotide sequences that encode novel paired basic amino acid converting enzymes (generically referred to as "PACE," with the two new enzymes being PACE 4 (SEQ ID No: 1)and 4.1 (SEQ ID No: 3)), to the production of PACE 4 and 4.1 in transformed cells, and to compositions comprising the PACE 4 and 4.1 enzymes. Materials and methods are also provided for the production of mature forms of proteins from heterologous precursor polypeptides using PACE 4 or 4.1, which are expressed in recombinant host cells.

2. Description of Related Art

Many eukaryotic proteins synthesized in bacteria fold incorrectly and, consequently, exhibit low specific activities. Post-translational proteolysis is a common mechanism required for the synthesis of biologically active proteins and peptides in all eukaryotes examined, including yeast (R. S. Fuller et al., (1988), *Ann. Rev. Physiol.* 50:345), invertebrates (R. H, Scheller et al. (1983), *Cell* 32:7), and mammalian cells (J. Douglass et al. (1984), *Ann. Rev. Biochem.* 53:665; W. S. Sossin et al. (1989), *Neuron* 2, 1407).

One of the early events in precursor protein maturation is endoproteolysis at the carboxyl side of pairs of basic amino acid sequences (e.g. -LysArg- and -ArgArg-). This kind of endoproteolytic cleavage was initially inferred from the sequences of several endocrine and neuroendocrine precursor proteins and was first proposed from studies of proinsulin (D. F. Steiner et al. (1968), *Science* 157:697; R. E. Chance et al. (1968), *Science* 161:165) and the ACTH/β-endorphin precursor, proopiomelanocortin (POMC)(M. Chretien and C. H. Li (1967), *Can. J. Biochem.* 45:1163). Subsequent studies have revealed a broad spectrum of precursor proteins that require endoproteolysis at pairs of basic amino acids to yield mature peptides including serum factors (A. K. Bentley et al. (1986), *Cell* 45:343), viral proteins (C. M. Rice et al. (1986), *Virology* 151:1; C. M. Rice et al. (1985), *Science* 229:726; J. M. McCune et al. (1988), *Cell* 53:55), growth factors (L. E. Gentry et al. (1988), *Mol. Cell Biol.* 8:4162; K. Sharples et al. (1987), *DNA* 6:239; M. Yanagisawa et al. (1988), *Nature* 332:41 1; and Gray et al. (1983), *Nature* 303:722) and receptors (Y. Yosirnasa (1988), *Science* 240:784).

Several candidate enzymes that are capable of cleaving at single or paired basic residues in vitro have been proposed as authentic mammalian precursor endoproteases. See, for example, Y. P. Loh and H. Gainer, in *Brain Peptides*, D. T. Krieger, M. J. Brownstein, J. B. Martin, Eds. (Wiley-Interscience, New York, 1983), pp.76–116; M. Chretien, et al. in *Cell Biology of the Secretory Process* (Karger, Basel, Switzerland, 1983), pp.214–246; A. J. Mason, et al. (1983), *Nature* 303:300; P. J. Isackson et al. (1987), *J. Cell. Biochem.* 33:65; I. Lindberg et al., (1984), *J. Neurochem* 42:141 1; J. A. Cromlish et al. (1986), *J. Biol. Chem.* 261:10850; K. Docherty et al. (1984), *J. Biol. Chem.* 259:6041; T. C. Chang and Y. P. Loh (1984), *Endocrinolog* 114,2092; B. P. Noe et al. (1984), *J. Cell. Biol.* 99:578; U. P. Loh (1986), *J. Biol. Chem.* 261:11949; H. W. Davidson et al. (1987), *Biochem. J.* 246:279; P. Gluschankof et al. (1987), *J. Biol. Chem.* 262:9615; C. Clamigrand et al. (1987), *Biochem* 26:6018; S. O. Brennan and R. J. Peach (1988), *FEBS Letters* 229:167; R. S. Fuller et al. (1989), *Proc. Natl. Acad. Sci. USA* 86:1434; K. Mizuno et al. (1989), *Biochem. Biophys. Res. Comm.* 159:305; I. C. Bathurst et al. (1987), *Science* 235:348; and G. Thomas et al. (1988), *Science* 241:226. However, none of these candidate activities have been shown to be a bona fide precursor cleaving endoprotease in vivo.

The yeast enzyme Kex2, a membrane-bound, $Ca^{2+}$-dependent serine protease (K. Mizuno et al. (1988), *Biochem. Biophys. Res. Commun.* 156:246; R. S. Fuller et al. (1989), *Proc. Natl. Acad. Sci. USA* 86:1434), has been considered to be a prototypic roprotein convertase. The Kex2 endoprotease, which is encoded by the KEX2 gene, functions late in the secretory pathway of Saccharomyces cerevisiae, and cleaves the polypeptide chains of prepro-killer toxin and prepro-a-factor at the paired basic amino acid sequences Lys-Arg and Arg-Arg (D. Julius et al. (1984), *Cell* 36:309). Furthermore, co-expression of the KEX2 gene with POMC in BSC40 cells (a cell line which is incapable of processing this peptide precursor) resulted in the generation, by proteolysis at pairs of basic amino acids, of authentic product peptides, including β-LPH and β-endorphin (Thomas et al. (1988), id.).

Two human DNA sequences, fur and PC2, share some structural homology with each other and with the KEX2 gene sequence. A. M. W. van den Ouweland et al. (1990), *Nucleic Acids Res.* 18:664 (presenting a cDNA coding sequence for fur; the cDNA sequence of FIG. 1 differs from this sequence in the region encoded by nucleotides 1–238); R. S. Fuller et al., *Science* 246:482 (1989); S. P. Smeekens (1990), *J. Biol. Chem.* 265:2997. The fur locus was initially identified by its proximity to the fes/fps proto-oncogene (A. J. M. Roebroek et al. (1986), *EMBO J.* 5:2197). PC2 was identified by amplification of a human insulinoma library by the polymerase chain reaction using KEX2-derived primers; it shares a partial homology with Kex2, especially in the putative active site domains (S. P. Smeekens and D. F. Steiner, (1990) *J. Biol. Chem.* 265:2997).

Another related cDNA encoding a protein variously called PC1 (Seidah et al. (1991) *Mol. Endocrinol.* 5:111–122) or PC3 (Smeekens et al. (1991) *Proc. Natl. Acad. Sci. USA* 88:340–344) has been isolated from murine pituitary cells. PC1/PC3 also shares amino acid similarity with KEX2, particularly in the putative catalytic domains.

Recently a finctional activity has been demonstrated for PC2 and PC1/PC3, using as a substrate the prohormone proopiomelanocortin (POMC). In the anterior lobe of the pituitary, POMC is processed to yield the hormones ACTH, β-lipotropin, and β-endorphin, while in the intermediate lobe it is processed to yield α-melanocyte stimulating hormone (α-MSH) and variant forms of ACTH and β-lipotropin. PC1/PC3 expressed in processing deficient cells cleaved POMC to give ACTH, but was less efficient in cleaving β-lipotropin to give β-endorphin. This is similar to the activity found in pituitary corticotrophic cells. Coexpression of PC2 and PC1/PC3 efficiently converted β-lipotropin, as is found in melanotrophic cells. Coexpression of POMC and PC2 in adrenomedullary chromaffin cells resulted in secretion of β-endorphin and α-MSH. Therefore PC1/PC3 and PC2 have differing substrate selectivities which yield physiologically relevant processed polypeptides.

Relevant Literature

AVIV, H., and LEDER, P. (1972). Purification of biologically active globin messenger RNA by chromatography on oligothymidylic acid-cellulose. *Proc. Natl. Acad. Sci. USA* 69, 1408–1412.

BARR, P. J. (1991). Mammalian subtilisins: The long-sought dibasic processing endoproteases. *Cell* 66, 1–3.

BARR, P. J., MASON, O. B., LANDSBERG, K. E., WONG, P. A., KIEFER, M. C., and BRAKE, A. J. (1991). cDNA and gene structure for a human subtilisin-like protease with cleavage specificity for paired basic amino acid residues. *DNA Cell Biol.* 10, 319–328.

BARR, P. J., THAYER, R. M., LAYBOURN, P., NAJARIAN, R. C., SEELA, F., and TOLAN, D. R. (1986). 7-Deaza-2'-Deoxyguanosine-5'-Triphosphate: Enhanced resolution in M13 dideoxy sequencing. *Biotechniques* 4, 428–432.

BENJANNET, S., RONDEAU, N., DAY, R., CHRETIEN, M., and SEIDAH, N. G. (1991). PC1 and PC2 are proprotein convertases capable of cleaving proopiomelanocortin at distinct pairs of basic residues. *Proc. Natl. Acad. Sci. USA* 88, 3564–3568.

BRESNAHAN, P. A., LEDUC, R., THOMAS, L., THORNER, J., GIBSON, H. L., BRAKE, A. J., BARR, P. J., and THOMAS, G. (1990). Human fur gene encodes a yeast KEX-2 like endoprotease that cleaves pro-β-NGF in vivo. *J. Cell. Biol.* 111, 2851–2859.

CHIRGWIN, J. M., PRZBYLA, A. E., MACDONALD, R. J., AND RUTTER, W. J. (1979). Isolation of biologically active ribonucleic acid from sources enriched in ribonuclease. *Biochemistry* 18, 5294–5299.

CHRISTIE, D. L., BATCHELOR, D. C., and PALMER, D. J. (1991). Identification of kex2 related proteases in chromaffin granules by partial amino acid sequence analysis. *J. Biol. Chem.* 266, 15679–15683.

FEINBERG, A. P., and VOGELSTEIN, B. (1984). A technique for radiolabeling DNA restriction endonuclease fragments to high specific activity. *Anal. Biochem.* 137, 266–267.

FREEMAN, G. J., CLAYBERGER, C., DEKRUYFF, R., ROSENBLUM, D. S., and CANTOR, H. (1983). Sequential expression of new gene programs in inducer T-cell clones. *Proc. Natl. Acad. Sci. USA* 80, 4094–4098.

FRICKER, L. D., DAS, B., and ANGELETTI, R. H. (1990). Identification of the pH-dependent membrane anchor of carboxypeptidase E (EC 3.4.17.10). *J. Biol. Chem.* 265, 2476–2482.

FULLER, R. S., BRAKE, A. J., and THORNER, J. (1989). Intracellular targeting and structural conservation of a prohormone-processing endoprotease. *Science* 246, 482–486.

GILBERT, W. (1985). Genes-in-pieces revisited. *Science* 228, 823–824.

HATSUZAWA, K., HOSAKA, M., NAKAGAWA, T., NAGASE, M., SHODA, A., MURAKAMI, K., and NAKAYAMA, K. (1990). Structure and expression of mouse furin, a yeast KEX2-related protease. *J. Biol. Chem.* 265, 22075–22078.

KIEFER, M. C., JOH, R. S., BAUER, D. M., and ZAPF, J. (1991). Molecular cloning of a new human insulin-like growth factor binding protein. *Biochem. Biophys. Res. Comm.* 176, 219–225.

KIEFER, M. C., MASIARZ, F. R, BAUER, D. M., and ZAPF, J. (1991). Identification and molecular cloning of two new 30-kDa insulin-like growth factor binding proteins isolated from adult human serum. *J. Biol. Chem.* 266, 9043–9049.

KORNER, J., CHUN, J., HARTER, D., and AXEL, R. (1991). Isolation and fimctional expression of a mammalian prohormone processing enzyme, murine prohormone convertase 1. *Proc. Natl. Acad. Sci. USA* 88, 6834–6838.

HOSAKA, M., NAGAHAMA, M., KIM, W.-S., WATANABE, T., HATSUZAWA, K., IKEMIZU, J., MURAKAMI, K., and NAKAYAMA, K. (1991). Arg-X-Lys/Arg-Arg motif as a signal for precursor cleavage catalyzed by furin within the constitutive secretory pathway. *J. Biol. Chem.* 266, 12127–12130.

LEHRACH, H., DIAMOND, D., WOZNEY, J. M., and BOEDIKER, H. (1977). RNA molecular weight determinations by gel electrophoresis under denaturing conditions, a critical re-examination. *Biochemistry* 16, 4743.

MISUMI, Y., ODA, K., FUJIWARA, T., TAKAMI, N., TASHIRO, K., and IKEHARA, Y. (1991). Functional expression of furin demonstrating its intracellular localization and endoprotease activity for processing of proalbumin and complement pro-C3. *J. Biol. Chem.* 266, 16954–16959.

PINKEL, D., LANDEGENT, J., COLLINS, C., FUSCOE, J., SEGRAVES, R., LUCAS, J., and GRAY, J. (1988). Fluorescence in situ hybridization with human chromosome specific libraries: Detection of trisomy 21 and translocations of chromosome 4. *Proc. Natl. Acad. Sci. USA* 85, 9138–9142.

ROEBROEK, A. J. M., SCHALKEN, J. A., BUSSEMAKERS, M. J. G., VAN HEERIKHUIZEN, H., ONNEKINK, C., DEBRUYNE, F. M. J., BLOEMERS, H. P. J., and VAN DE VEN, W. J. M. (1986). Characterization of human c-fes/fps reveals a new transcription unit (fur) in the immediately upstream region of the proto-oncogene. *Mol. Biol. Rep.* 11, 117–125.

SAIKI, R. K., SCHARF, S., FALOONA, F., MULLIS, K. B., HORN, G. T., ERLICH, H. A., and ARNHEIM, N. (1985). Enzymatic amplification of β-Globin genomic sequences and restriction site analysis for diagnosis of sickle cell anemia. *Science* 230, 1350–1354.

SAMBROOK, J., MANIATIS, T., FRITSCH, E.F. (1989). Molecular Cloning: A Laboratory Manual. (Cold Spring Harbor Laboratory, Cold Spring Harbor, N.Y.).

SCHALKEN, J. A., ROEBROEK, A. J. M., OOMEN, P. P. C. A., WAGENAAR, S. S C., DEBRUYNE, F. M. J., BLOEMERS, H. P. J., and VAN DE VEN, W. J. M. (1987). fur Gene expression as a discriminating marker for small cell and nonsmall cell lung carcinomas. *J. Clin. Invest.* 80, 1545–1549.

SEIDAH, N. G., GASPAR, L., MION, P., MARCINKIEWICZ, M., MBIKAY, M., and CHRETIEN, M. (1990). cDNA sequence of two distinct pituitary proteins homologous to Kex2 and furin gene products: Tissue-specific mRNAs encoding candidates for prohornone processing proteinases. *DNA Cell Biol.* 9, 415–424.

SHENNAN, K. 1. J., SEAL, A. J., SMEEKENS, S. P., STEINER, D. F., and DOCHERTY, K. (1991). Site-directed mutagenesis and expression of PC2 in microinjected xenopus oocytes. *J. Biol. Chem.*

SMEEKENS, S. P., AVRUCH, A. S., LAMENDOLA, J., CHAN, S. J., and STEINER, D. F. (1991). Identification of a cDNA encoding a second putative prohormone convertase related to PC2 in AtT20 cells and islets of Langerhans. *Proc. Natl. Acad. Sci. USA* 88, 340–344.

SMEEKENS, S. P., and STEINER, D. F. (1990). Identification of a human insulinoma cDNA encoding a novel mammalian protein structurally related to the yeast dibasic processing protease Kex2. *J. Biol. Chem.* 265, 2997–3000.

THOMAS, P. S., (1980). Hybridization of denatured RNA and small DNA fragments transferred to nitrocellulose. *Proc. Natl. Acad. Sci. USA* 77, 5201.

THOMAS, L., LEDUC, R., THORNE, B. A., SMEEKENS, S. P., STEINER, D. F., and THOMAS, G. (1991). KEX2-like endoproteases PC2 and PC3 accurately cleave a model prohormone in mammalian cells: Evidence for a common core of neuroendocrine processing enzymes. *Proc. Natl. Acad. Sci. USA* 88, 5297–5301.

TOMKINSON, B. and JONSSON, A.-K. (1990). Characterization of cDNA for human tripeptidyl peptidase 11: The N-terminal part of the enzyme is similar to subtilisin. *Biochem.* 30, 168–174.

VAN DE VEN, W. J. M., VOORBERG;, J., FONTIJIN, R., PANNEKOEK, H., VAN DEN OUWELAND, A. M. W., VAN DUIJNHOVEN, H. L. P., ROEBROEK, A. J. M., and SIEZEN, R. J. (1990). Furin is a subtilisin-like proprotein processing enzyme in higher eukaryotes. *Mol. Biol. Rep.* 14, 265–275.

VON HEIJNE, G. (1986). A new method for predicting signal sequence cleavage sites. *Nucl. Acids Res.* 14, 4683–4690.

WANG, P. H., DO, Y. S., MACAULAY, L, SHINAGAWA, T., ANDERSON, P. W., BAXTER, J. D., and HSUEH, W. A. (1991). Identification of renal cathepsin B as a human prorenin-processing enzyme. 266, 12633–12638.

WISE, R. J., BARR, P. J., WONG, P. A., KIEFER, M. C., BRAKE, A. J., and KAUFMAN, R. J. (1990). Expression of a human proprotein processing enzyme: Correct cleavage of the von Willebrand precursor at a paired basic amino acid site. *Proc. Nati. Acad. Sci. USA* 87, 9378–9382.

YANISCH-PERRON, C., VIEIRA, L., and MESSING, J. (1985). Improved M13 phage cloning vectors and host strains. Nucleotide sequences of the M13 mp 18 and pUC19 vectors. *Gene* 33, 103–119.

ZAPF, J., KIEFER, M., MERRYWEATHER, J., MASIARZ, F., BAUER, D., BORN, W., FISCHER, J. A., and FROESCH, E. F. (1990). Isolation from adult human serum of four insulin-like growth factor (IGF) binding proteins and molecular cloning of one of them that is increased by IGF1 administration and in extra-pancreatic tumor hypoglycemia. *J. Biol. Chem.* 265, 14892–14898.

SUMMARY OF THE INVENTION

Recombinant polynucleotides are provided for the expression of a novel mammalian endopeptidase, PACE 4, and its alternative form, PACE 4.1, which are involved in the production of mature polypeptides from precursor polypeptides by cleavage at pairs of basic amino acids (e.g., -LysArg-, -LysLys-, and -ArgArg-). These recombinant polynucleotides can be used for enhanced intracellular or extracellular production of PACE 4 and 4.1 in transformed cells. Additionally, efficient conversion of co-expressed heterologous polypeptides having processing sites recognized by PACE 4 or 4.1 can produce desired mature forms of those polypeptides.

Purified PACE 4 and 4.1 are also provided. These have utility for commercial and pharmaceutical purposes.

The present invention includes vectors, transformed mammalian, insect, and microorganism cells, methods for producing PACE 4 and 4.1, methods for expressing and secreting a desired mature polypeptide from a heterologous precursor polypeptide using PACE 4 or 4.1, purified PACE 4 and 4.1, a pharmaceutical preparation containing PACE 4 or 4.1, and therapeutic methods involving administration of PACE 4 or 4.1, or inhibitors of PACE 4 and 4.1.

DESCRIPION OF THE DRAWING

Figure 1A:
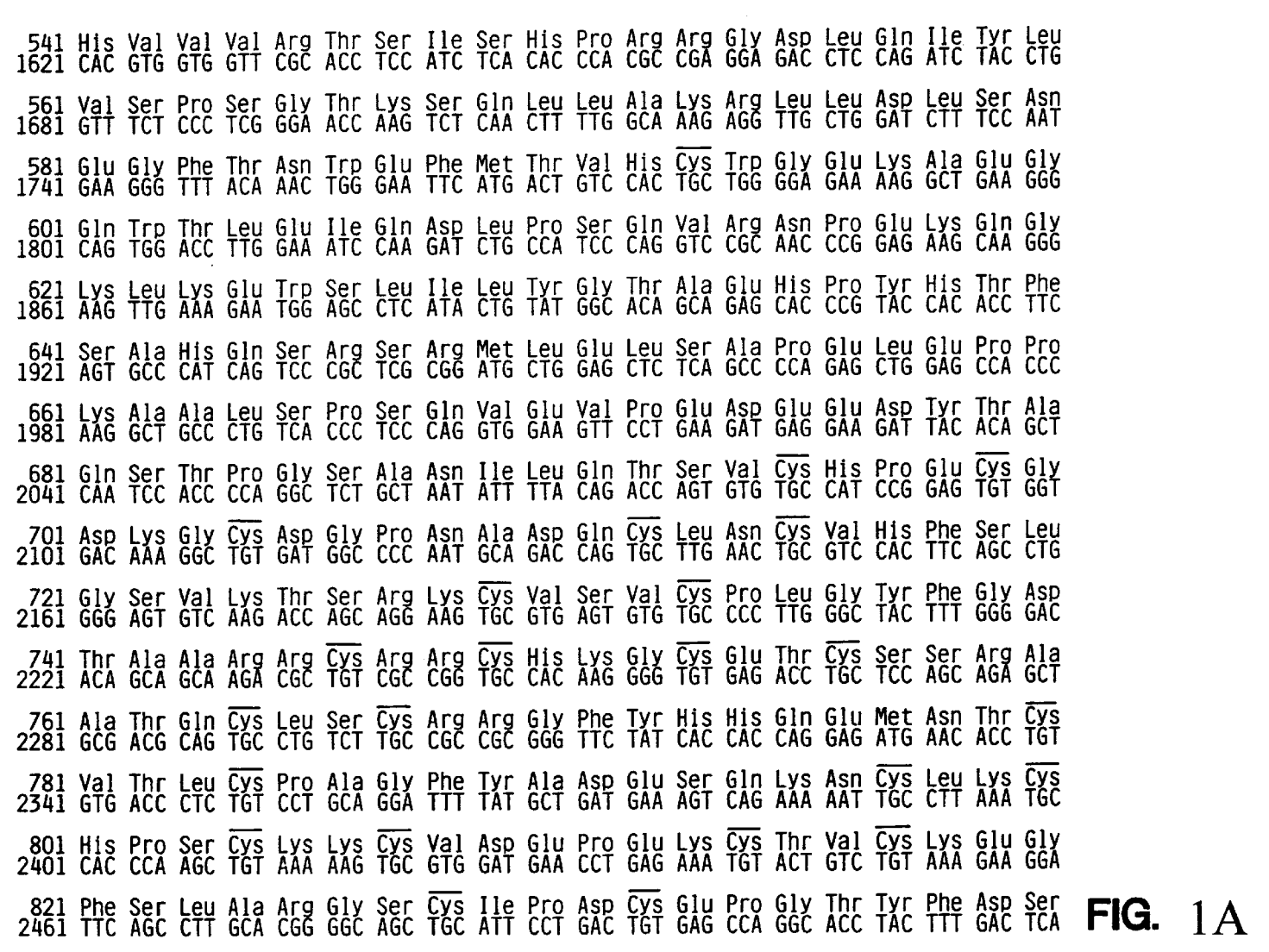
Figure 1A-1:
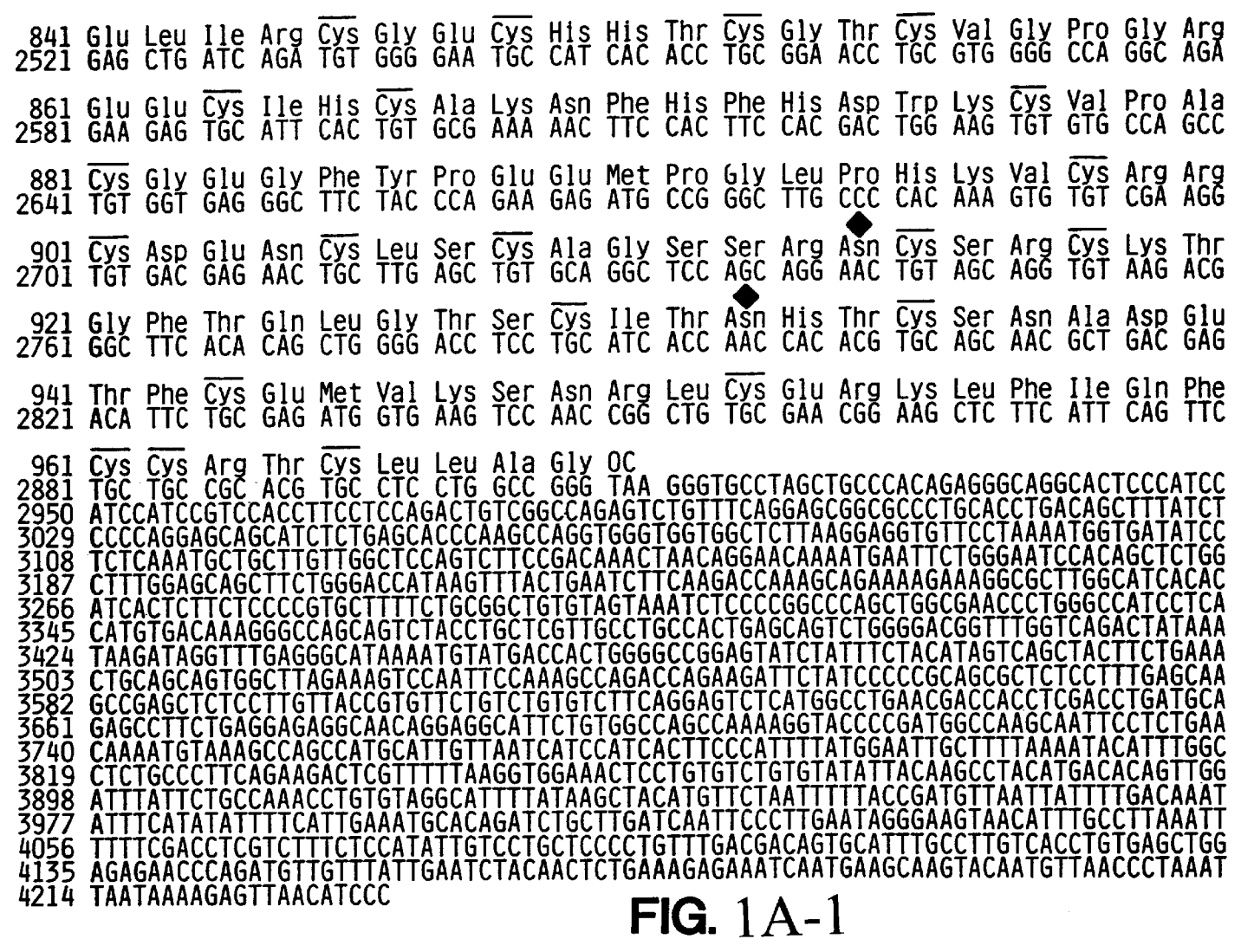
Figure 1B:
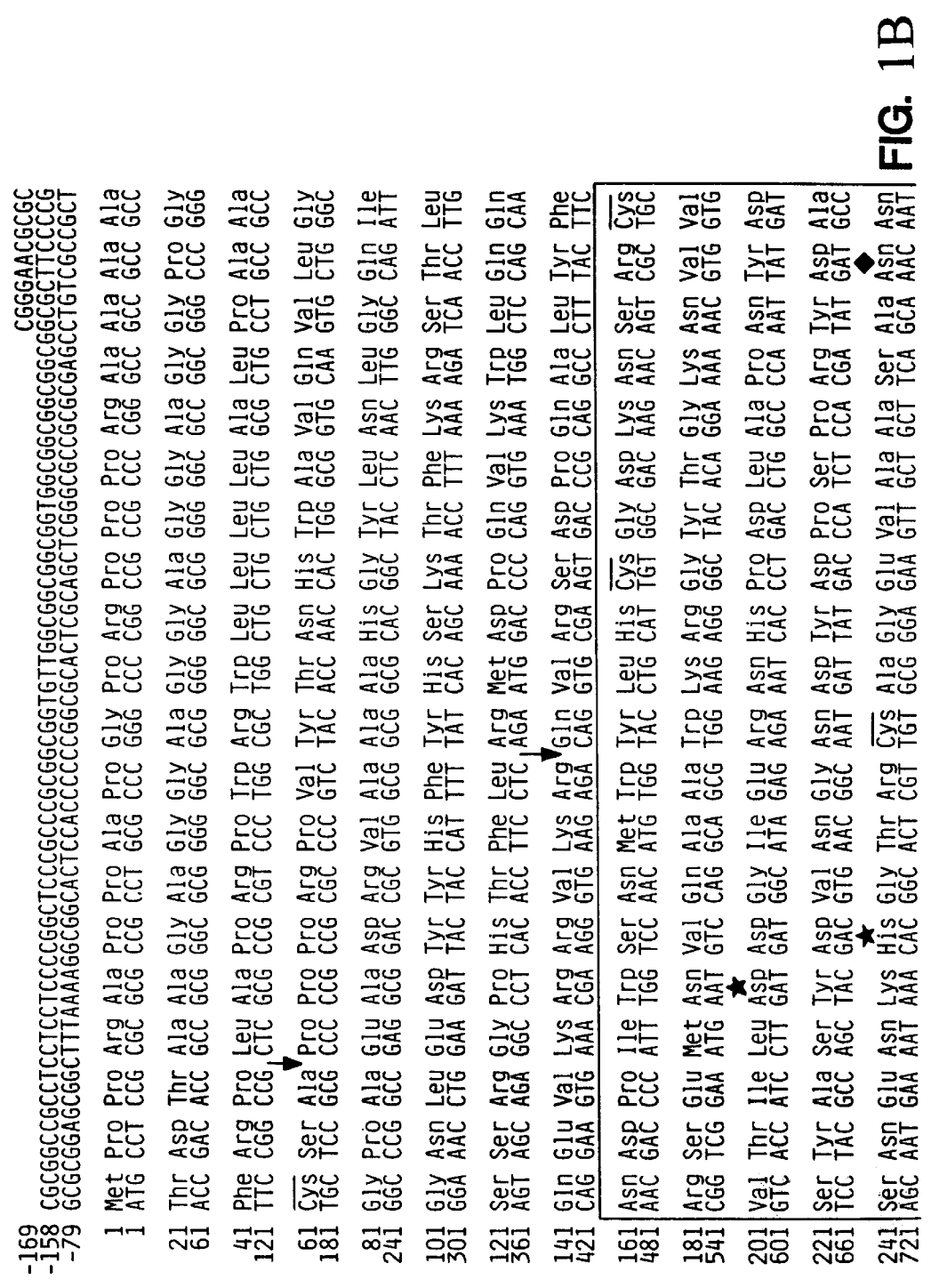
Figure 1B-1:
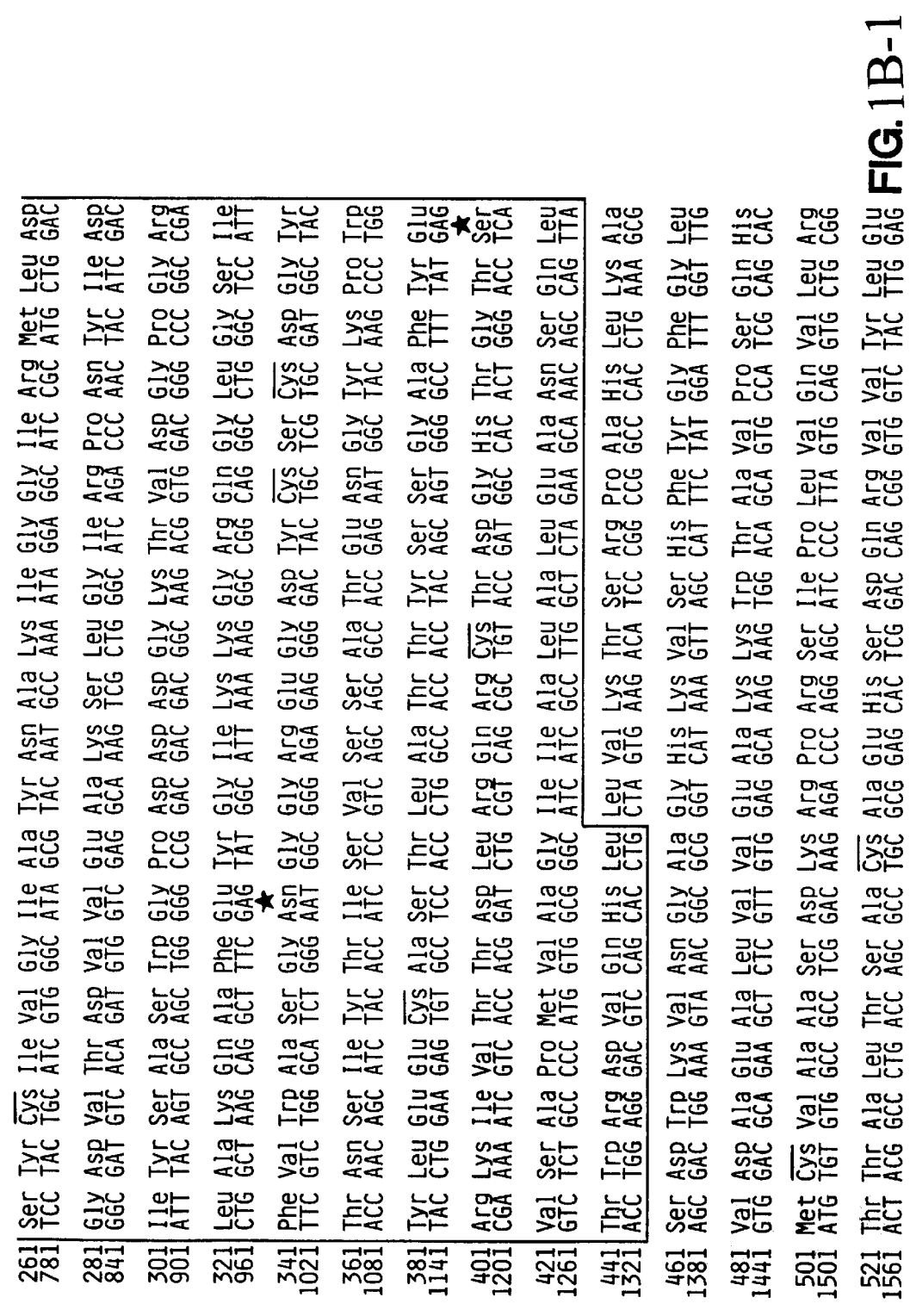

FIG. 1 shows the composite cDNA sequence encoding PACE 4 (SEQ ID No: 1), and the amino acid sequence of the translation product (SEQ ID No: 2)encoded therein.

FIG. 2 shows the composite cDNA sequence encoding the alternate splicing region of PACE 4.1 (SEQ ID No: 3), and the amino acid sequence of the translation product encoded therein (SEQ ID No: 4). Shown are the additional cDNA sequence encoding 16 amino acids, termination codon, and 3'-untranslated region which comprise the truncated cDNA and encoded protease amino acid sequence of PACE 4.1. The sequence of PACE 4.1 is identical to that of PACE 4 through Lys 471. The beginning of the divergence in cDNA sequence is indicated by an arrow.

FIG. 3 shows the DNA sequence of the homolog of exon 12 of the furin/PACE gene (SEQ ID No: 5) (Barr et al., 1991). This sequence contains the intron/exon splice junction for commitment to either PACE 4 or PACE 4.1 mRNA. This exon sequence corresponds to PACE 4 residues Ser 473 to Pro 510.

FIG. 4 provides a restriction map, clone diagrams, and composite diagram for PACE 4. The composite diagram indicates the amino terminal signal sequence by a shaded box, and the remainder of the coding region by the hatched box. Individual clones are identified above the composite diagram. Restriction endonucleases are abbreviated as follows: B, BamHI; G, BglII; R, EcoRI; Sm, SmaI; Sp, SphI. Each clone has synthetic EcoRI and BglII sites at the 5' and 3' termini.

Figure 5:
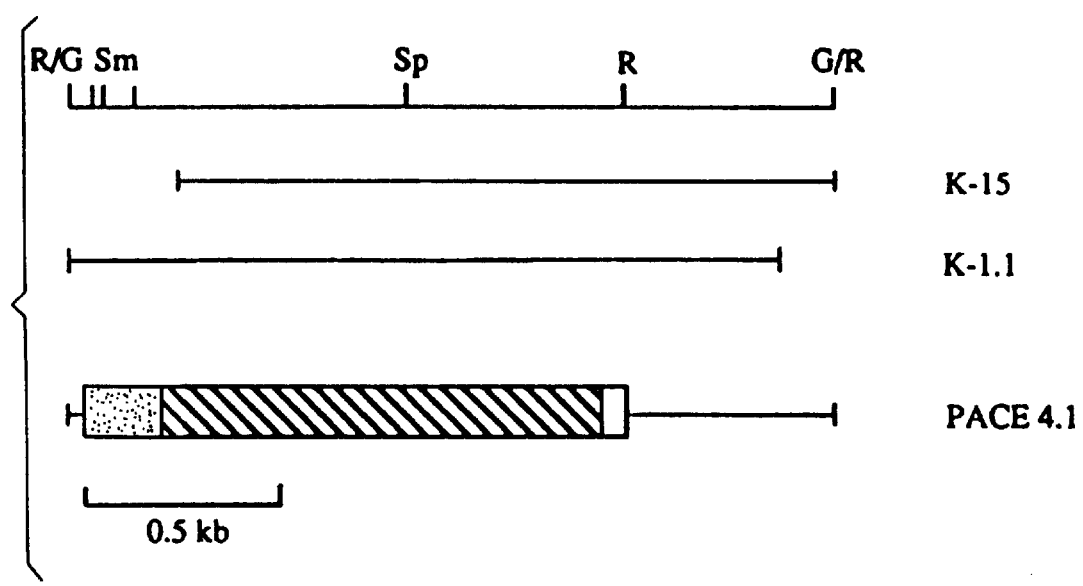

FIG. 5 provides a restriction map, clone diagrams, and composite diagram for PACE 4.1. The composite diagram indicates the amino terminal signal sequence by a shaded box, and the remainder of the coding region by the hatched box. Individual clones are identified above the composite diagram. Restriction endonucleases are abbreviated as follows: B, BamHI; G, BglII; R, EcoRi; Sm, SmaI; Sp, SphI. Each clone has synthetic EcoRI and BglII sites at the 5' and 3' termini.

Figure 6:
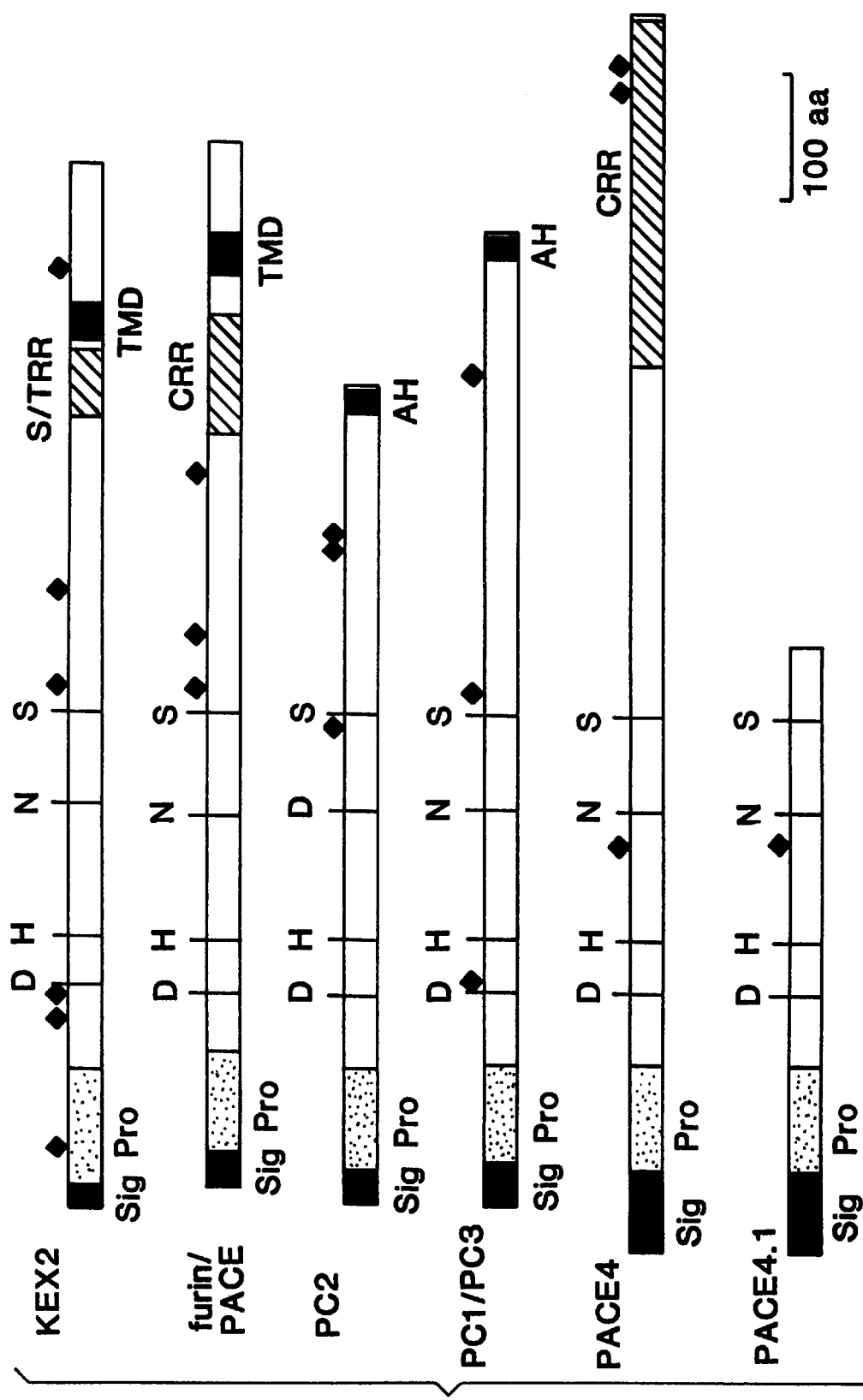
Figure 8A:
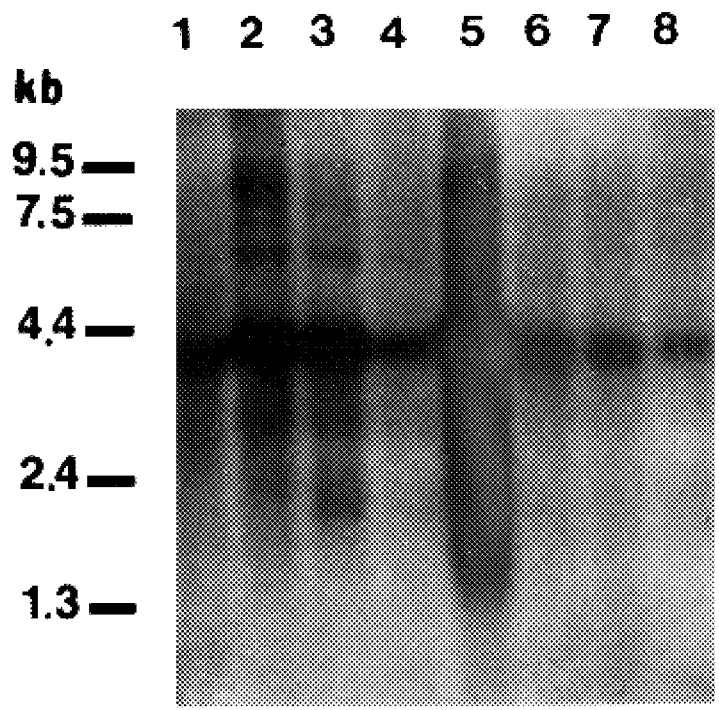
Figure 8B:
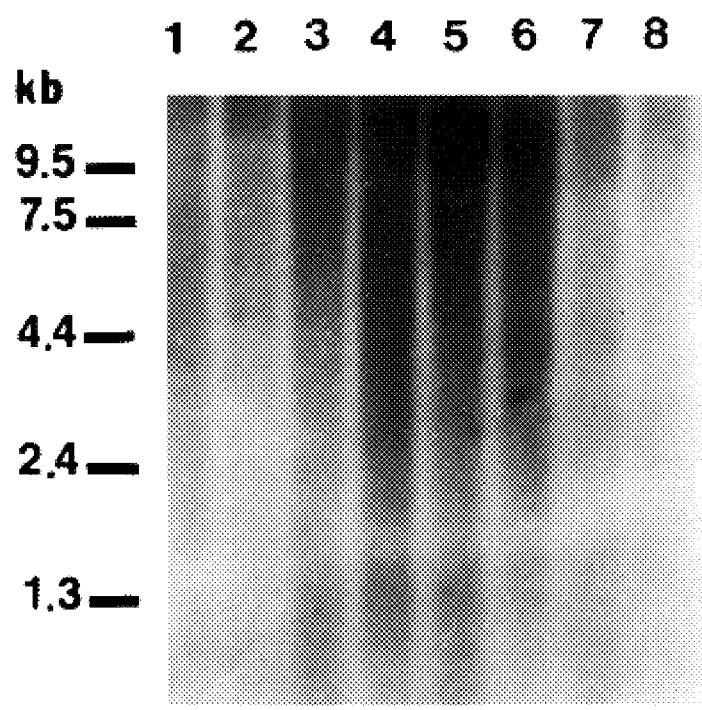
Figure 8C:
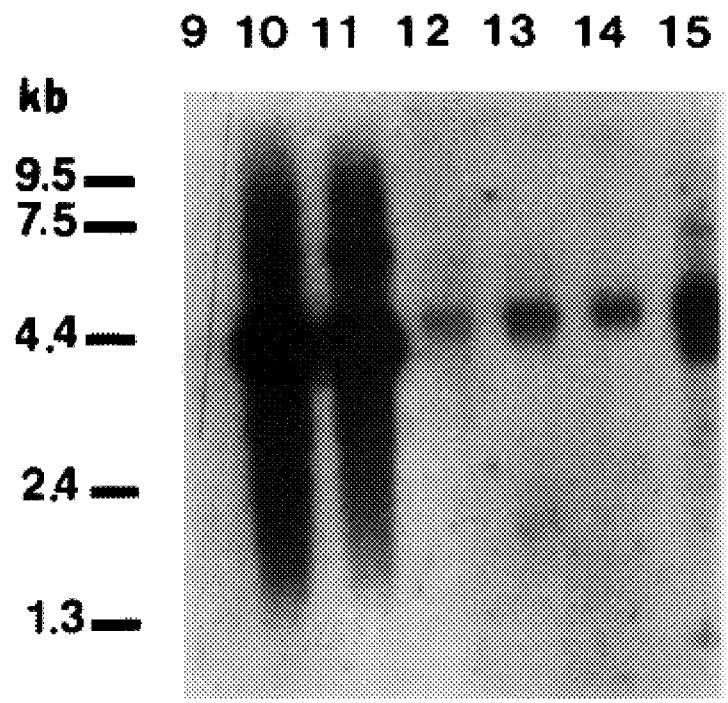
Figure 8D:
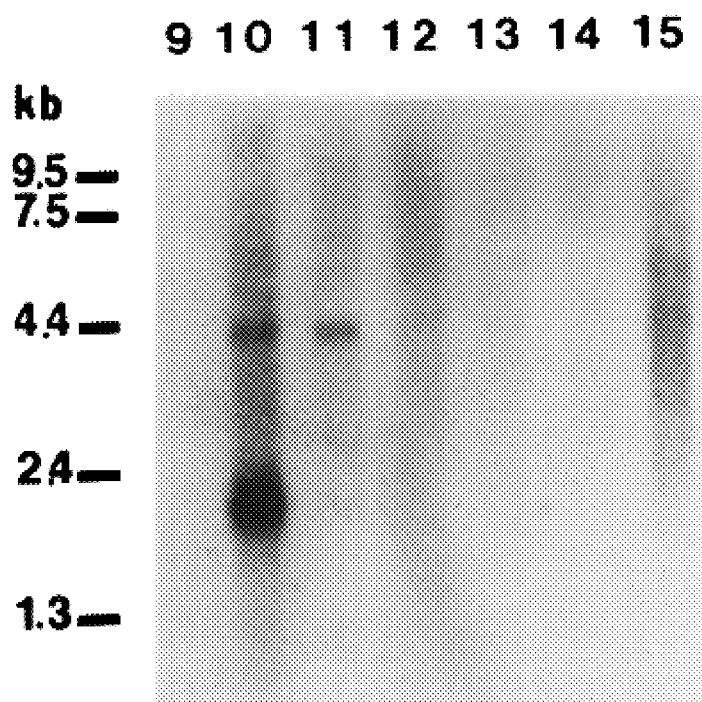
Figure 9A:
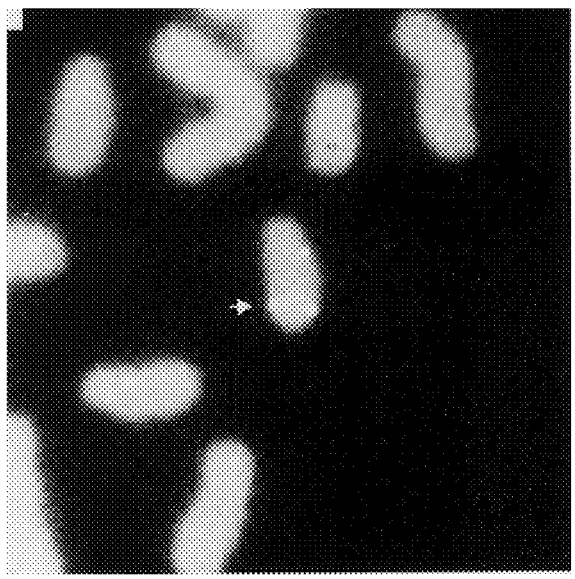
Figure 9B:
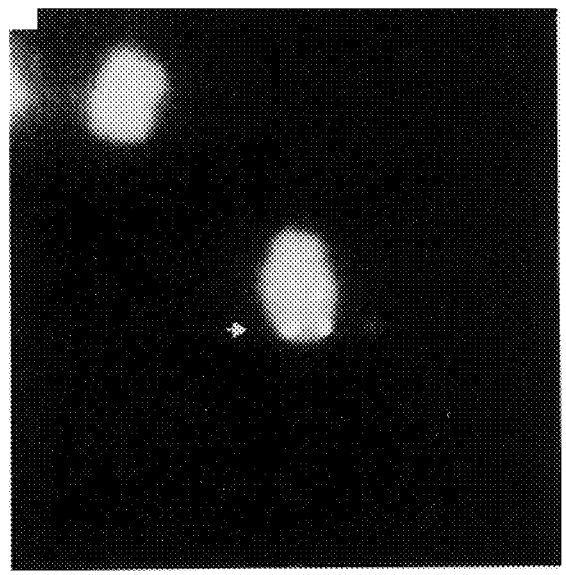
Figure 9C:
Figure 9D:
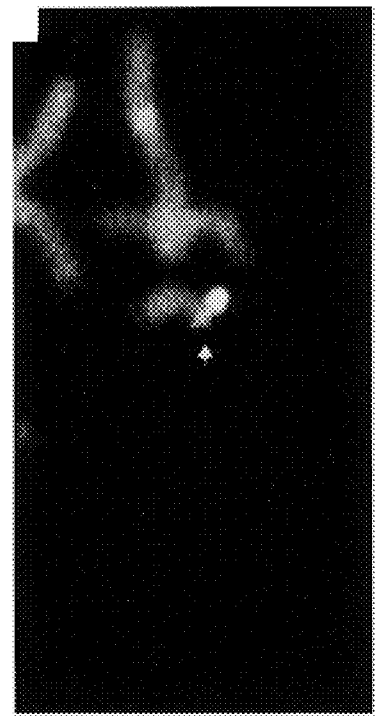
Figure 9E:
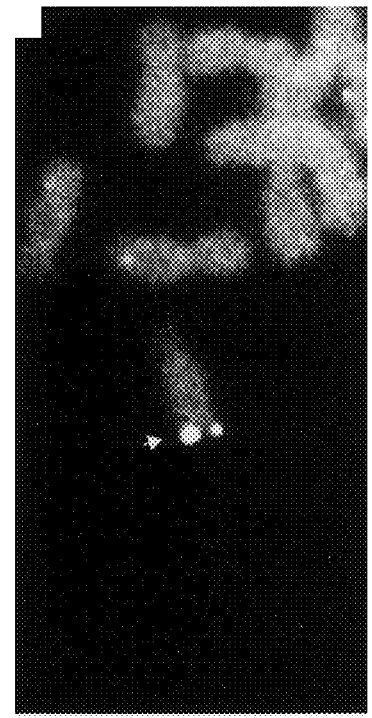

FIG. 6 is a domain map of PACE 4 and 4.1, together with comparative maps for other dibasic endoproteases KEX2, furin/PACE, PC2, and PC1/PC3. Active site Asp, His, Asn (Asp), and Ser residues are indicated as D, H, N (D), and S, respectively. Potential glycosylation sites are indicated by a diamond. Putative signal peptides (Sig), membrane-binding amphipathic helices (AH), and transmembrane domains (TM) are indicated by solid boxes. Cysteine-rich (CRR) and serine/threonine-rich (S/TRR) regions are indicated by hatched boxes. Proprotein regions are indicated by shaded boxes.

Figure 7:
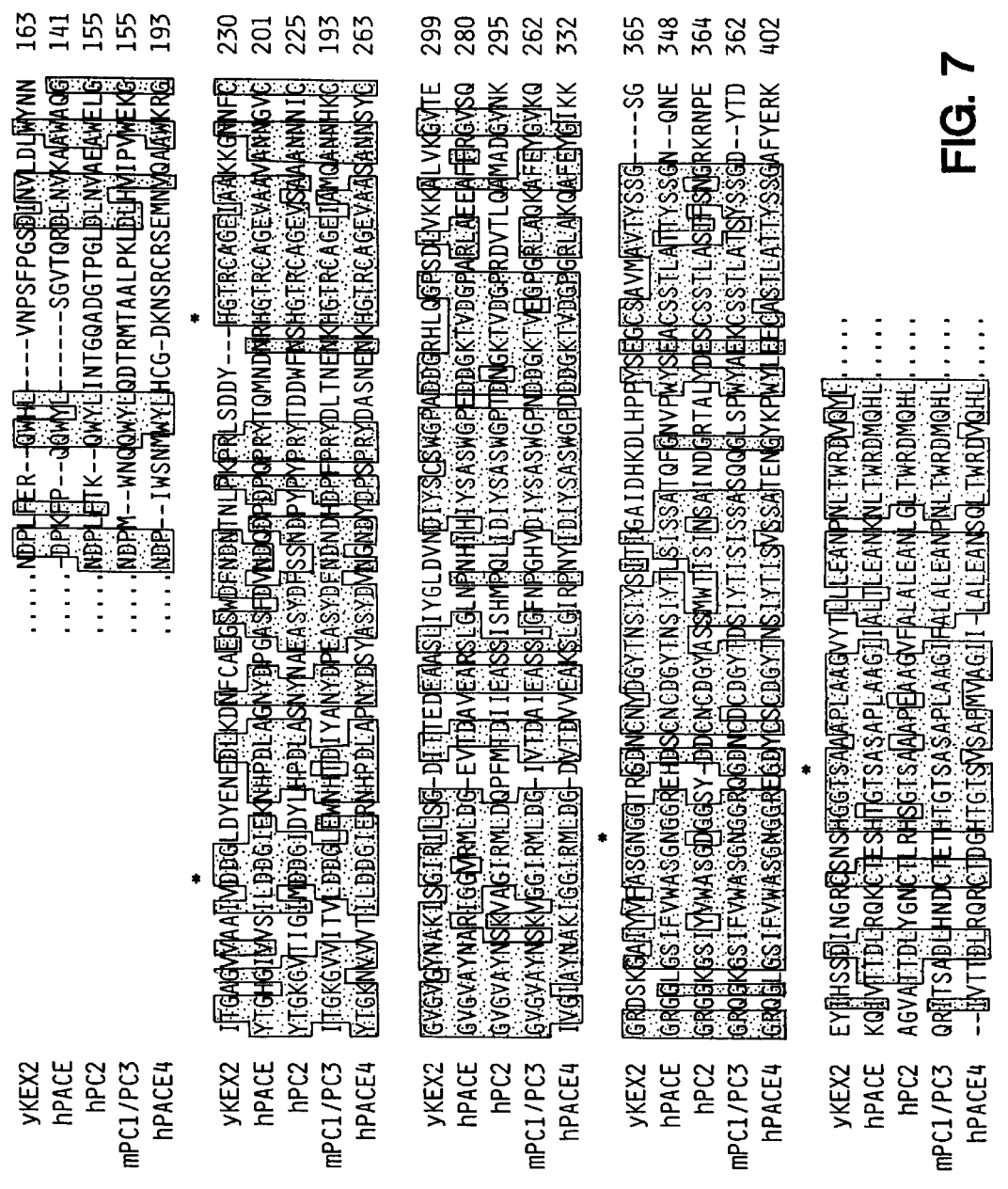

FIG. 7 shows a comparison among the amino acid sequences of the catalytic domains of PACE 4 and 4.1 (human) (SEQ ID No: 11) and other dibasic endoproteases KEX2 (yeast) (SEQ ID No: 7), furin/PACE (human) (SEQ ID No: 8), PC2 (human) (SEQ ID No: 9), and PC1/PC3 (mouse) (SEQ ID No: 10). Amino acids that are identical among three or more proteases are indicated.

FIGS. 8A–8D show Northern blot analysis of PACE 4 and 4.1. The blots in panels A and B contain human poly(A)+ RNAs from various tissues, while those in panels C and D contain poly(A)+ RNAs from human or hamster cultured cell lines. Blots were hybridized with a PACE 4 specific probe (panels A and C) or a PACE 4.1 specific probe (panels B and D).

FIGS. 9A–9E show in situ hybridization of cosmid DNA to metaphase chromosomes as revealed by fluorescence of FITC labelled fur and Texas Red labelled PACE 4 gene probes.

DETAILED DESCRIPTION OF THE INVENTION

I. Definitions

As used herein, the term "PACE" is an acronym for paired basic amino acid converting enzyme. An enzyme belonging to the PACE family is a subtilisin-like endopeptidase, i.e., a propeptide-cleaving enzyme, which exhibits specificity for cleavage at basic residues of a polypeptide, e.g., -lys-arg-, -arg-arg, or -lys-lys-; is stimulated by calcium ions; and is inhibited by phenylmethyl sulfonyl fluoride (PMSF).

A CDNA that encodes a novel form of PACE, referred to herein as PACE 4, is presented in FIG. 1 (SEQ ID No: 1). PACE 4 is derived from an animal cell, more specifically from a human cell. Previous applications, including U.S. Application Nos. 07/620,859, filed Nov. 29, 1990; 07/621,443, filed Nov. 29, 1990; and 07/621,457, filed Nov. 30, 1990, herein incorporated by reference, disclose the isolation of a gene encoding a different form of PACE, also isolated from human cells. The present invention demonstrates that other forms of PACE exist and that they can be produced artifically. Thus, "PACE 4" refers to any of the naturally occurring forms, including the PACE 4 precursor protein shown in FIG. 1 (SEQ ID No: 2), and various processed forms, including the mature PACE 4 polypeptide and modified proteins that have the properties of natural-sequence PACE 4. "Natural-sequence PACE 4" refers to the specific molecule having the sequence set forth in FIG. 1 (SEQ ID No: 2)and the fragments and derivatives thereof defined in this specification. Polypeptide fragments that maintain the catalytic specificity of that enzyme are encompassed by the general term PACE 4. Additionally, analogs of PACE 4 are included within the definition of PACE 4, and include truncated polypeptides (including fragments) and PACE 4-like polypeptides, e.g., mutants in which there are variations in the amino acid sequence that retain catalytic activity and preferably have a homology of at least 80%, more preferably 90%, and most preferably 95%, with the corresponding region of the PACE 4 sequence of FIG. 1 (SEQ ID No: 2). Typically, such analogs differ by only 1, 2, 3, or 4 amino acids. Examples include polypeptides with minor amino acid variations from the natural amino acid sequence of PACE 4; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on the enzymatic activity, especially if the replacement does not involve an amino acid at the active site of the PACE-like polypeptide. As discussed elsewhere in this specification in detail, a PACE 4 molecule of a variant type, referred to as PACE 4.1, has a sequence partially identical with the sequence of PACE 4, and exhibits similar enzymatic properties. PACE 4.1 is produced by alternate splicing of mRNA, and encompasses the catalytic domain of PACE 4 truncated on the C-terminal side, to which is added an additional 16 amino acids comprising a novel C-terminus.

Utilizing the sequence data in FIG. 1, as well as the denoted characteristics of a PACE molecule in general and those of PACE 4 and 4.1 in particular, it is within the skill of the art to obtain other PACE 4 or 4.1 polypeptides, or other DNA sequences encoding PACE 4 or 4.1. For example, the structural gene can be manipulated by varying individual nucleotides, while retaining the correct amino acid(s), or varying the nucleotides, so as to modify the amino acids, without loss of enzymatic activity. Nucleotides can be substituted, inserted, or deleted by known techniques, including, for example, in vitro mutagenesis and primer repair. The structural gene can be truncated at its 3'-terminus and/or its 5'-terminus while retaining its endopeptidase activity. For example, PACE 4 as encoded in FIG. 1 (SEQ ID No: 2) contains a cysteine-rich region (CRR), which it may be desirable to delete. It also may be desirable to remove the region encoding the signal sequence, and/or to replace it with a heterologous sequence. It may also be desirable to ligate a portion of the PACE 4 or 4.1 sequence (particularly that which includes the catalytic domain) to a heterologous coding sequence, and thus to create a fusion peptide with the enzymatic specificity of PACE 4.

In designing such modifications, it is expected that changes to nonconserved regions of the PACE-type structure will have relatively smaller effects on activity, whereas changes in the conserved regions, and particularly in or near the catalytic active site domains D, H, and S, are expected to produce larger effects.

The comparison among catalytic domain sequences of yeast KEX2 (SEQ ID No: 7), human PACE (SEQ ID No: 8), human PC2 (SEQ ID No: 9), mouse PC1/PC3 (SEQ ID No: 10), and human PACE 4 (SEQ ID No: 11), given in FIG. 7, provides guidance on amino acid substitutions which are compatible with catalytic activity. Amino acid residues which are conserved among PACE 4 and at least three of the four related proteins are important for good catalytic activity and are not expected to be candidates for substitution. A residue which shows conservative variations among PACE 4 and at least two of the four related proteins is expected to be capable of similar conservative substitution of the PACE 4 sequence. Similarly, a residue which varies nonconservatively among PACE 4 and at least three of the four related proteins is expected to be capable of either conservative or nonconservative substitution. When designing substitutions to the PACE 4 or 4.1 sequence, replacement by an amino acid which is found in the comparable aligned position of one of the four related proteins is especially preferred.

In addition to the above, other open reading frames (ORFs) or structural genes encoding PACE 4 or 4.1 can be obtained and/or created from cDNA libraries from other animal cell sources.

As used herein, the term "polypeptide" refers to a polymer of amino acids and does not refer to a specific length of the product; thus, peptides, oligopeptides, and proteins are included within the definition of polypeptide. This term also does not exclude post-expression modifications of the polypeptide, for example, glycosylations, acetylations, phosphorylations and the like. Included within the definition are, for example, polypeptides containing one or more analogs of an amino acid (including, for example, unnatural amino acids) and polypeptides with substituted linkages, as well as other modifications known in the art, both naturally occurring and non-naturally occuring.

The term "precursor polypeptide" denotes an expressed polypeptide which normally undergoes one or more post-translational proteolytic cleavages to yield a biologically active mature polypeptide. Included within the term "precursor polypeptide" are "prepropolypeptides" and "propolypeptides."

A "prepeptide" is the portion of a precursor polypeptide which is removed by "signal peptidase" cleavage during translocation of the polypeptide into the endoplasmic reticulum. The "prepeptide" region is usually at or near the amino terminus.

A "propeptide" is the portion of a precursor polypeptide which is removed by a "propolypeptide convertase" or "endopeptidase" (for example, Kex2 and PACE) during the maturation process of the polypeptide. Many proteins, such as plasma proteins, hormones, neuropeptides, and growth factors, are translated with an additional "propeptide" region located to the carboxy side of the prepeptide region. After cleavage of the prepeptide, the "propeptide" segment is cleaved by a site-specific endopeptidase contributing to the maturation of the polypeptide. A "mature" form of a polypeptide has had a prepeptide and/or propeptide region removed.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A polypeptide of the invention is not necessarily translated from a designated nucleic acid sequence, for example, the sequence in FIG. 1. It can be generated in any manner, including, for example, chemical synthesis, expression of a recombinant expression system, or isolation from a cell. A recombinant or derivative polypeptide of the invention can include one or more analogs of amino acids or unnatural amino acids in its sequence. Methods of inserting analogs of amino acids into a sequence are known in the art. It also can include one or more labels, which are known to those of skill in the art.

The term "recombinant polynucleotide" as used herein intends a polynucleotide of genomic, cDNA, semisynthetic, or synthetic origin which, by virtue of its origin or manipulation (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This can include selectable markers.

A "vector" is a replicon in which a recombinant polynucleotide segment is attached, so as to bring about the replication and/or expression of the attached segment "Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaxyotes, generally, such control sequences include promoters and transcription termination sequence. The term "control sequences" is intended to include, at a rninimum, all components whose presence is necessary for expression, and can also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region can represent a portion of a coding sequence or a total coding sequence.

A "coding sequence" is a polynucleotide sequence which is translated into a polypeptide, usually via MRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Recombinant host cells," "host cells," "cells," "cell lines," "cell cultures," and other such terms denoting mammalian, insect, or microorganism cells that can be, or have been, used as recipients for a recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

"Mammalian cells" are cells that are from a member of the Class Mammalia, and microorganism cells and insect cells are specifically excluded from this group.

Insect cells and compatible vectors which are useful as recombinant expression systems are known in the art, and include, for example, insect expression and transfer vectors derived from the baculovirus Auto rapha califomica nuclear polyhedrosis virus (hereinafter "AcNPV" or "baculovirus"), which is a helper-independent, viral expression vector. Viral expression vectors derived from this system usually use the strong viral polyhedrin gene promoter to drive expression of heterologous genes.

As used herein, the term "microorganism" includes prokaryotic and eukaryotic microbial species such as bacteria and fungi, the latter including yeast and filamentous fingi; the term "microorganism" specifically excludes mammalian cells and insect cells.

"Transformation," as used herein, refers to the insertion of an exogenous polynucleotide into a host cell, irrespective of the method used for the insertion, for example, direct uptake, transfection, transduction, infection, or electroporation. The exogenous polynucleotide can be maintained as a non-integrated vector, for example, a plasmid, or alternatively, can be integrated into the host genome.

"Substantially pure" as used herein means a level of purity which enables the practice of the appropriate function. With respect to PACE 4 or 4.1 polypeptides, these are in general substantially pure if the levels of competing and interfering proteolytic enzymes are low enough to permit the activity of PACE 4 or 4.1 to generate the major reaction products. Preferably this means that the PACE 4 or 4.1 will account for at least 90% of the endoprotease activity, more preferably at least 95% of endoprotease activity, and most preferably at least 99% of endoprotease activity.

As used herein, an "oligonucleotide" is a polynucleotide containing from 10 to approximately 200 bases, usually less than about 60 bases, and which is usefull inter alia as a probe or diagnostic reagent for identifying the presence of a complementary nucleotide sequence.

II. General Modes for Carrying Out the Invention

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al, MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D.M. Weir and C. C. Blackwell eds 1986). All patents, patent applications, and publications mentioned herein, both supra and infra, are hereby incorporated herein by reference.

III. Specific Modes for Carrying Out the Invention

DNA sequences, constructs (vectors) containing the DNA sequences, and mammalian, insect, and microorganism hosts containing these constructs are provided for herein. These compositions have utility in processes for producing PACE 4 and 4.1 and for producing mature polypeptides from heterologous precursor polypeptides. Also provided are compositions comprising substantially pure PACE 4 or 4.1, and pharmaceutical compositions comprising PACE 4 or 4.1. Additionally, methods for producing PACE 4 and 4.1, methods for inhibiting blood coagulation and for reducing blood pressure, and also methods for producing a desired mature polypeptide are included in the present invention.

Methods for producing a desired mature polypeptide can include the following techniques. First, a vector coding for both PACE 4 or 4.1 and the heterologous precursor polypeptide can be inserted into a host cell, or two vectors coding, respectively, for PACE 4 or 4.1 and the heterologous precursor polypeptide, can be inserted into a host. Furthermore, two transformed hosts can be employed wherein one host expresses PACE 4 or 4.1 and the other host expresses the heterologous precursor polypeptide; these hosts can be co-cultured whereby PACE processes the heterologous precursor into the mature polypeptide in the medium.

Another method employs a single transformed host cell expressing PACE 4 or 4.1, whereby PACE 4 or 4.1 is isolated from the cell and can be used in in vitro processing of a heterologous precursor polypeptide. The PACE 4 or 4.1 can be immobilized by, e.g., packing into or attaching to a column or other useful support configuration. Soluble or immobilized recombinant PACE 4 or 4.1 can be used as an added reagent to extracellular (or conditioned) media where a precursor product is secreted from the cell in which it is expressed.

In some instances, it may be desirable to have a plurality of copies, two or more, of the gene expressing the expression product precursor in relation to the PACE 4 or 4.1 gene, or vice versa. This can be achieved in a variety of ways. For example, one can use separate vectors, where the vector having either PACE 4/4.1 or the heterologous precursor polypeptide has a higher copy number than the other vector. In this situation, it would be desirable to have different markers on the two vectors, so as to ensure the continued maintenance of the vectors in the mammalian host. Alternatively, one could employ two transcriptional regulatory regions having different rates of transcriptional initiation, providing for enhanced expression of either the PACE 4 or 4.1 gene or the heterologous precursor polypeptide relative to the other gene. As another alternative, one can use different promoters, where one promoter provides for a low level of constitutive expression of either PACE or the heterologous precursor polypeptide, while the second promoter provides for a high level of induced expression of the other product.

Examples of precursor polypeptides include, but are not limited to, transforming growth factor (TGF) beta and its superfamily, including inhibin and activin; bone morphogenic proteins (BMP); insulin and relaxin; coagulation factors, such as von Willebrand factor; growth factors, such as platelet derived growth factor (PDGF) and nerve growth factor (NGF); and virus polypeptides, including those from cytomegalovirus (CMV), hepatitis delta virus (HDV), hepatitis C virus (HCV), human immunodeficiency virus (HIV), and herpes simplex virus (HSV). Any precursor polypeptide with at least one dibasic cleavage site is a candidate for this aspect of the present invention.

The PACE 4 or 4.1 gene or a fragment thereof can be expressed in a mammalian, insect, or microorganism host. The polynucleotide encoding PACE is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes.

A suitable expression vector is one that is compatible with the desired function (e.g., transient expression, long term expression, integration, replication, amplification) and in which the control elements are compatible with the host cell.

Expression in Mammalian Cells

Vectors suitable for replication in mammalian cells are known in the art, and can include viral replicons, or sequences that ensure integration of the sequence encoding PACE into the host genome. Suitable vectors can include, for example, those derived from simian virus SV40, retroviruses, bovine papilloma virus, vaccinia virus, and adenovirus.

A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vectors that greatly facilitate the construction of recombinant viruses have been described (see, for example, Mackett et al. (1984), Chalrabarti et al. (1985); Moss (1987)). Expression of the heterologous polypeptide then occurs in cells or individuals which are immunized with the live recombinant vaccinia virus.

Such suitable mammalian expression vectors usually contain one or more eukaryotic transcription units that are capable of expression in mammalian cells. The transcription unit is comprised of at least a promoter element to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

The optional presence of an enhancer element (enhancer), combined with the promoter elements described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter [Maniatis et al. (1987) Science 236:1237; Alberts et al. (1989) *Molecular Biology of the Cell,* 2nd ed.]. Enhancer elements derived from viruses may be particularly useful, because they typically have a broader host range. Examples useful in mammalian cells include the SV40 early gene enhancer [Dijkema et al (1985) EMBO J. 4:761] and the enhancer/promoters derived from the long terminal repeat (LTR) of the Rous Sarcoma Virus [Gorman et al. (1982b) *Proc. Natl. Acad. Sci.* 79:6777]and from human cytomegalovirus [Boshart et al. (1985) Cell 41:521]. Additionally, some enhancers are regulatable and become active only in the presence of an inducer, such as a hormone or metal ion [Sassone-Corsi and Borelli (1986) Trends Genet. 2:215; Maniatis et al. (1987) Science 236:1237].

In addition, the transcription unit can also be comprised of a termination sequence and poly(A) addition sequences which are operably linked to the PACE 4 or 4.1 coding sequence. The transcription unit can also be comprised of an enhancer sequence which increases the expression of PACE 4 or 4.1.

Sequences that cause amplification of the gene may also be desirable, as are sequences which encode selectable markers. Selectable markers for mammalian cells are known in the art, and include for example, thymidine kinase, dihydrofolate reductase (together with methotrexate as a DEFR amplifier), aminoglycoside phosphotransferase, hygromycin B phosphotransferase, asparagine synthetase, adenosine deaminase, metallothionien, and antibiotic resistant genes such as neomycin.

The vector that encodes PACE can be used for transformation of a suitable mammalian host cell. Transformation can be by any known method for introducing polynucleotides into a host cell, including, for example packaging the polynucleotide in a virus and transducing a host cell with the virus or by tranfection procedures known in the art, as exemplified by U.S. Pat. Nos. 4,399,216; 4,912,040; 4,740,461; 4,959,455 (these patents are incorporated herein by reference). The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Expression in Insect Cells

In the case of expression in insect cells, generally the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol* 42:177) and a procaryotic ampicillin-resistance (amp gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector can also have a second domain called an enhancer, which, if present, is usually distal to the structural gene. Expression can be either regulated or constitutive.

Expression in Microorganisms

Fungal expression systems can utilize both yeast and filamentous fungi hosts. Examples of filamentous fingi expression systems are Aspergillus, as described in EPO Pub. No. 357 127 (published Mar. 7, 1990), and Acremonium chrysogenum, described in EPO Pub. No. 376 266 published Jul. 4, 1990).

A yeast expression system can typically include one or more of the following: a promoter sequence, fusion partner sequence, leader sequence, transcription termination sequence. These elements can be combined into an expression cassette, which can be maintained in a replicon, preferably with a selectable marker.

A yeast promoter is any DNA sequence capable of binding yeast RNA polymerase and initiating the downstream (3') transcription of a coding sequence (e.g., structural gene) into MRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter can also have a second domain called an upstream activator sequence (UAS), which, if present, is usually distal to the structural gene. The UAS permits regulated (inducible) expression. Constitutive expression occurs in the absence of a UAS. Regulated expression can be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(E.P.O. Pub. No. 329203). The yeast PH05 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter can be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO15 genes, combined with the transcriptional activation region of a glycolytic enzyme gene such as GAP or PyK(E.P.O. Pub. No. 164556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast Saccharomyces cerevisiae," in: *Plasmids of Medical. Environmental and Commercial Importance* (eds. K. N. Timmis and A. Puhler); Mercerau-Puigalon et al. (1980) *Gene* 11:163; Panthier et al. (1980) *Curr. Genet.* 2:109;].

The PACE 4 gene or a fragment thereof can be expressed intracellularly in yeast. A promoter sequence can be directly linked with the PACE 4 gene or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of the PACE gene or fragment. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of the PACE 4 gene or fragment thereof and expressed in yeast. The DNA sequence at the junction of the two amino acid sequences may or may not encode a cleavable site. See e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the PACE 4 or 4.1 polypeptide. Through this method, therefore, a mature PACE 4 or 4.1 polypeptide can be isolated (P.C.T. WO 88/024066). Alternatively, PACE 4 or 4.1 polypeptides can also be secreted from the cell into the growth media by creating chimeric DNA molecules that encode a fusion protein comprised of a leader sequence fragment that provides for secretion in yeast of the PACE 4 or 4.1 polypeptides. Preferably, there are processing sites encoded between the leader fragment and the PACE gene or fragment thereof that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 12873; J.P.O. Pub. No.

62,096,086) and the A-factor gene (U.S. Pat. No. 4,588, 684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; E.P.O. Pub. No. 324274). Additional leaders employing an alpha-factor leader fragment that provides for secretion include hybrid alpha-factor leaders made with a presequence of a first yeast, but a pro-region from a second yeast alphafactor. (See e.g., P.C.T. WO 89/02463.)

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs or cassettes are often maintained in a replicon, such as an extrachromosomal element (e.g., plasmids) capable of stable maintenance in a host, such as yeast or bacteria. The replicon can have two replication systems, thus allowing it to be maintained, for example, in yeast for expression and in a procaryotic host for cloning and amplification. Examples of such yeast-bacteria shuttle vectors include YEp24 [Botstein et al. (1979) *Gene* 8:17–24], pC1/1 [Brake et al. (1984) *Proc. Natl. Acad. Sci USA* 81:4642–4646], and YRp17 [Stinchcomb et al. (1982) *J. Mol. Biol.* 158:157]. In addition, a replicon can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the PACE polypeptides. See e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228–245]. An integrating vector can be directed to a specific locus in yeast by selecting the appropriate homologous sequence for inclusion in the vector. See Orr-Weaver et al, supra. One or more expression construct can integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression vectors can contain selectable markers to allow for the selection of yeast strans that have been transformed. Selectable markers can include biosynthetic genes that can be expressed in the yeast host, such as ADE2, HIS4, LEU2, TRP1 and ALG7 and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are typically comprised of a selectable marker that is either maintained in a replicon or developed into an integrating vector, as described above.

Expression and transfornation vectors, either extrachromosomal replicons or integrating vectors, have been developed for transformation into many yeasts. For example, expression vectors have been developed for, inter alia, the following yeasts: Candida albicans [Kurtz, et al. (1986) *Mol. Cell. Biol.* 6:142], Candida maltosa [Kunze, et al. 91985) *J. Basic Microbiol.* 25:141]. Hansenula polymorpha [Gleeson, et al. (1986) *J. Gen. Microbiol.* 132:3459; Roggenkamp et al. (1986) *Mol. Gen. Genet.* 202:302], Kluyveromyces fragilis [Das, et al (1984) *J. Bacteriol.* 158:1165], Kluyveromyces lactis [De Louvencourt et al. (1983) *J. Bacteriol.* 154:737; Van den Berg et al. (1990) *Bio/Technology* 8:135], Pichia guillerimondii [Kunze et al. (1985) *J. Basic Microbiol.* 25:141], Pichia pastoris [Cregg, et al. (1985) *Mol. Cell. Biol.* 5:3376; U.S. Pat. Nos. 4,837,148 and 4,929,555], Saccharomyces cerevisiae [Hinnen et al. (1978) *Proc. Natl. Acad. Sci. USA* 75:1929; Ito et al. (1983) *J. Bacteriol.* 153:163], Schizosaccharomyces pombe [Beach and Nurse (1981) *Nature* 300:706], and Yarrowia lipolytica [Davidow, et al. (1985) *Curr. Genet.* 10:380471 Gaillardin, et al. (1985) *Curr. Genet.* 10:49].

Methods of introducing exogenous DNA into yeast hosts are well-known in the art, and typically include either the transformation of spheroplasts or of intact yeast cells treated with alkali cations. Transformation procedures usually vary with the yeast species to be transfonned. See e.g., [Kurtz et al. (1986) *Mol. Cell. Biol.* 6:142; Kunze et al. (1985) *J. Basic Microbiol.* 25:141; Candida]; [Gleeson et al. (1986) *J. Gen. Microbiol.* 132:3459; Roggenkamp et al (1986) *Mol. Gen. Genet.* 202:302; Hansenula]; [Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces]; [Cregg et al. (1985) *Mol. Cell. Biol.* 5:3376; Kunze et al. (1985) *J. Basic Microbiol.* 25:141; U.S. Pat. Nos. 4,837,148 and 4,929,555, Pichia]; [Hinnen et al. (1978) *Proc. Natl. Acad. Sci. USA* 75;1929; Ito et al. (1983) *J. Bacteriol.* 153:163 Saccharomces]; [Beach and Nurse (1981) *Nature* 300:706; Schizosaccharomyces]; [Davidow et al. (1985) *Curr. Genet.* 10:39; Gaillardinetal. (1985) *Curr. Genet.* 10:49; Yarrowia].

Additionally, the PACE 4 gene or a fragment thereof can be expressed in a bacterial system. Therein, a bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; E.P.O. Pub. Nos. 36,776 and 121,775]. The β-lactamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (E.P.O. Pub. No. 267,851).

In addition to a functioning promoter sequence, an efficient ribosome binding site is also useful for the expression of the PACE gene or fragment thereof in prokaryotes. In *E. coli* the ribosome binding site is called the Shine-Dalgarno (SD) sequence and includes an initiation codon (ATG) and a sequence 3–9 nucleotides in length located 3–11 nucleotides upstream of the initiation codon [Shine et al (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Exression* (ed. R.F. Goldberger)].

To express eukaryotic genes and prokaryotic genes with weak ribosome-binding site [Sambrook et al. (1989) "Expression of cloned genes in *Escherichia coli*." In *Molecular Cloning: A Laboratorv Manual*].

PACE 4 or 4.1 can be expressed intracellularly. A promoter sequence can be directly linked with the PACE 4 gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terrninal peptidase (E.P.O. Pub. No. 219,237).

Fusion proteins provide an alternative to direct expression. Typically, a DNA sequence encoding the N-term portion of an endogenous bacterial protein, or other stable protein, is fused to the 5' end of heterologous PACE 4 or 4.1 coding sequences. Upon expression, this construct will provide a fusion of the two amino acid sequences. For example, the bacteriophage lambda cell gene can be linked at the 5' terminus of the PACE gene or fragment thereof and expressed in bacteria The resulting fusion protein preferably retains a site for a processing enzyme (factor Xa) to cleave the bacteriophage protein from the PACE gene or fragment thereof [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoffet al. (1989) *J. Gen. Microbiol.* 135:11], and Chey [E.P.O. Pub. No. 324,647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the PACE polypeptide. Through this method, mature PACE polypeptides can be isolated [Miller et al. (1989) *Bio/Technology* 7:698].

Alternatively, PACE 4 or 4.1 polypeptides can also be secreted from the cell by creating chimeric DNA molecules that encode a fusion protein comprised of a signal peptide sequence fragment that provides for secretion of the PACE 4 or 4.1 polypeptides in bacteria [U.S. Pat. No. 4,336,336]. The signal sequence fragment typically encodes a signal peptide comprised of hydrophobic amino acids which direct the secretion of the protein from the cell. The protein is either secreted into the growth media (gram-positive bacteria) or into the periplasmic spece, located between the inner and outer membrane of the cell (gram-negative bacteria). Preferably there are processing sites, which can be cleaved either in vivo or in vitro encoded between the signal peptide fragment and the PACE 4 or 4.1 polypeptide.

DNA encoding suitable signal sequences can be derived from genes for secreted bacterial proteins, such as the E.coli outer membrane protein gene (ompA) [Masui et al. (1983), in: *Experimental Manipulation of Gene Expression*; Ghrayeb et al. (1984) EMBO J. 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacilus* strains can be used to secrete heterologous proteins from *B. subtilis* [Palva et al. (1982) *Proc. Natl. Acad. Sci. USA* 79:5582; E.P.O. Pub. No. 244,042].

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E.coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector can be selected, depending upon the effect of the vector and the PACE 4 or 4.1 polypeptide on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bactedrial chromosome. For example, integrating vectors constructed with DNA from various *Bacillus* strains integrate into the *Bacillus* chromosome (E.P.O. Pub. No. 127, 328). Integrating vectors can also be comprised of bacteriophage or transposon sequences.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many bacteria. For example, expression vectors have been developed for, *inter alia*, the following bacteria: *Bacillus subtilis* [Palva et al. (1982) *Proc. Natl. Acad. Sci. USA* 79:5582; E.P.O. Pub. Nos. 36,259 and 63,953; P.C.T. WO 84/04541], *Escherichia coli* [Shimatake et al. (1981) *Nature* 292:128; Amann et al. (1985) *Gene* 40:183; Studier et al. (1986) *J. Mol. Biol.* 189:113; E.P.O. Pub. Nos. 36,776, 136,829 and 136,907; U.K. Patent Application Serial No.8418273], *Streptococcus cremoris* [Powell et al. (1988) *Appl. Environ. Microbiol.* 54:655] *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; E.P.O. Pub. Nos. 36,259 and 63,953; P.C.T. WO 84/04541, *Bacillus*], [Miller et al. (1988) *Proc. Natl. Acad. Sci.* 85:856; Wang et al (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation," in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Sonkuti et al. (1987) *Proc. 4th Evr. Cong. Biotechnology* 1:412, *Streptococcus*].

Expression and Detection of expressed PACE 4 or 4.1

In order to obtain PACE 4 or 4.1 expression, recombinant host cells derived from the transformants are incubated under conditions which allow expression of the recombinant PACE encoding sequence. These conditions will vary, depending upon the host cell selected. However, the conditions are readily ascertainable to those of ordinary skill in the art, based upon what is known in the art.

Detection of PACE 4 or 4.1 expressed in the transformed host cell can be accomplished by several methods. For example, detection can be by enzymatic activity (or increased enzymatic activity or increased longevity of enzymatic activity) using fluorogenic substrates which are comprised of a dibasic cleavage site for which PACE is specific. PACE can also be detected by its immunological reactivity with anti-PACE antibodies.

Therapeutic Aspects of PACE 4 or 4.1

PACE 4 and 4.1 mRNAs are expressed at relatively high levels in the kidney, as demonstrated by northern blots (FIG. 8). Since physiological conversion of prorenin to renin occurs in the kidney, PACE 4 and 4.1 are candidates for in vivo prorenin processing enzymes. Furthermore, PACE 4 and 4.1 convert prorenin to renin, a process which results in elevation of blood pressure. Blockers of PACE 4 and 4.1 enzymatic activity therefore limit blood pressure increase. PACE 4 and 4.1 inhibitors have therapeutic utility in treating high blood pressure. PACE 4 and 4.1 appear likely to have physiological effects on endogenous proteins that possess dibasic cleavage sites. Any such effects can be exploited for therapeutic purposes.

Oligonucleotide Probes

Probes based upon the PACE 4 gene sequence or its complementary sequence are useful for detecting the presence of nucleotide sequences encoding PACE 4 or related polypeptides. Such probes can be used for example to detect PACE 4 mRNA transcription in tissues, or to identify the PACE 4 encoding bands on gels, or to identify structurally related homologous proteins. Since PACE 4 and 4.1 are known to share regions of homology with other dibasic cleaving endoproteases such as KEX2, PC1/PC3, PC2, and furin/PACE, probes based upon regions of the PACE 4 sequence which are not shared with these other endoproteases are especially useful in discriminating PACE 4 related sequences from the other endoproteases.

A comparison of the amino acid sequence of PACE 4 (SEQ ID No: 11) with these other endoproteases is given in FIG. 7. Within the catalytic domain, the regions from amino acids 164 to 168, 172 to 189, 239 to 243, and 397 to 404 are seen to be unique to PACE 4. Other unique sequences exist in the noncatalytic domain of PACE 4 and 4.1. PACE 4 contains a large cysteine-rich region (CRR) within its C-terminal region which is unique to this protease, although a smaller CRR exists within furin/PACE. PACE 4 and 4.1 also have extended signal peptide sequences, compared to the other proteases in the family. In addition, PACE 4 and 4.1 have neither the classical transmembrane anchor domain of furin/PACE, nor the amphipathic helix (AH) surface membrane anchor proposed for PC2 and PC1/PC3. Thus significant sequence differences from other PACE family proteases exist in the noncatalytic domains of PACE 4 and 4.1.

Probes based upon the nucleotide sequences corresponding to the above unique amino acid sequences are expected to be selective for PACE 4 and 4.1 and previously unknown homologues. A probe based on at least 15, and more preferably at least 20 consecutive nucleotides from the unique PACE 4 sequences and optionally in part upon the common endoprotease conserved regions, or alternatively the simultaneous or consecutive use of two probes based upon the unique and conserved regions respectively, permits identification of PACE 4 related endoproteases which are distinct from those identifiable by probes based only on sequences shared by PACE 4 and the known related protease sequences of FIG. 7.

In light of the present disclosure, numerous embodiments within the scope of the claims will be apparent to those of ordinary skill in the art. The following experimental section is intended to be merely illustrative and does not limit the present scope in any way.

Example 1

PCR Identification of PACE 4⁺cDNA Clones

To identify and clone new members of the human subtilisin-like protease gene family, degenerate PCR primers were designed and synthesized corresponding to stretches of amino acids in the highly conserved catalytic domains of yeast KEX2, human PACE, human PC2, and mouse PC1/PC3. These included regions containing the active site Asp (DDGI) and the active site His (HGTRC).

Oligonucleotide Synthesis

Oligonucleotide adaptors, probes, and primers were synthesized as previously described (Kiefer et al., 1991). The two consensus PCR primers used to identify PACE 4 were a sense primer consisting of a mixture of 16 23-mers (5'-AGATCTGAATTCGA(C/T)GA(C/T)GGXAT-3') (SEQ ID No: 12) and an antisense primer consisting of a mixture of 64 27-mers (5'-AGATCTAAGCTTACACC(G/T) XGTXCC(A/G)TG-3') (SEQ ID No: 13), where X denotes all four deoxynucleotides. The PACE 4 probes used to screen the Ost4 cDNA library were a 24mer, (5'-TATTCATTGCCGTTCACGTCGTAG-3') (SEQ ID No: 14) and a 22mer (5'-GCTGGCATCATATCGTGGAGAT-3') (SEQ ID No: 15) that were derived from the sequence complementary to the PACE 4 PCR product (see below).

Polymerase Chain Reactions (PCR)

PCR was performed as described (Saiki et al, 1985) with modifications (Kiefer et al., 1991). The reactions were performed using the PCR primers described above at 8 mM and human osteosarcoma, liver or kidney (293) cDNA at 0.1–1 ng/ml. PCR products migrating between 120–170 base pairs on a 7% acrylamide gel were excised, subcloned into M13 and sequenced.

Construction and Screening of CDNA and Genomic DNA Libraries

A 293 cDNA library was constructed in ZAPII as described by Zapf et al. (1990). 6×10⁷ independent recombinant clones were obtained. The HepG2 cDNA library (Zapf et al., 1990) and the human osteosarcoma (Ost4) cDNA library (Kiefer et al., 1991) have been described previously. An oriented cDNA library was constructed in the yeast expression vector pAB23BXN using poly (A)⁺mRNA isolated from the human liver cell line HEPG2. pAB23BXN is a derivative of pAB23BX (D. Schild et al. (1990), *Proc. Natl. Acad. Sci. USA* 87:2916) into which a synthetic polylinker, that contained Bst X1 and Not 1 sites, was inserted for unidirectional cDNA cloning.

Approximately 300,000 recombinant phage from the Ost4 library were screened as described (Kiefer et al., 1991) using the two PACE 4 oligonucleotide probes. The HepG2 and 293 cDNA libraries were plated as above and screened with a ~1.0 Kb BglII DNA fragment derived from the 5' end of the Ost4 cDNA clone, Os-1.

The 293 cDNA library was subsequently further screened with a ~500 bp EcoRI fragment derived from the 3' end of the 293 cDNA clone, K-15, and a synthetic oligonucleotide (PACE2.115) derived from a sequence complementary to the 5' end of PACE 4 cDNA and including the initiation codon (5'-GGAGGCATAGCGGCGAC-3') (SEQ ID No: 16). The cDNA probes were labeled as described (Feinberg and Vogelstein, 1984) and were hybridized to filters under conditions described above for the oligonucleotide probes except that the hybridization solution contained 40% formamide. The filters were washed twice for 20 min,. in 0.2×SSC, 0.1 % SDS at 65° C.

To obtain the human PACE 4 gene, 600,000 colonies from a human genomic DNA library cloned in the cosmid vector pWE15 (Stratagene, San Diego, Calif.) were plated and screened with a ~1.0 Kb BglII DNA fragment from the 5' end of the Os-1 cDNA clone and subsequently with a ~1.1 kb EcoRI DNA fragment from the 3' end of the L2—1 cDNA clone (FIG. 4). Two overlapping clones of ~35–40 kb were obtained which hybridized to the 5' probe (PACE 4-COS 3) and 3' probe (PACE 4-COS 8.1).

Plasmid and Cosmid Isolation, Subcloning and DNA Sequencing

Standard procedures for the isolation and manipulation of DNA are from Sambrook et al. (1989). Plasmid DNA was propagated in *E.coli* strains HB101, D1210 or XL-1 Blue (Stratagene). DNA sequencing was performed by the dideoxy chain termination method (Sanger et aL, 1977) using M13 primers as well as specific internal primers. Ambiguous regions were resolved using 7-deaza-2'-deoxyguanosine-5'-triphosphate (Barr et al., 1986) and Sequenase (U.S. Biochemicals).

After PCR amplification of cDNA reverse transcribed from poly(A)⁺RNA isolated from human cell lines HEPG2 and 293 and from human osteosarcoma cells, the expected products (circa 150 base pairs) were gel purified, pooled and subcloned into the M13 mp18 DNA sequencing vector. Sequence analysis of 10 PCR products revealed one sequence that was predicted to encode a stretch of 37 amino acids displaying 30–60% sequence identity to yeast KEX2, human furin/PACE, human PC2 and mouse PC1/PC3.

In an attempt to isolate a full length cDNA encoding the new human subtilisin-like protease, an osteosarcoma (Ost4) cDNA library was screened with an oligonucleotide probe derived from the sequence of the 37 amino acid encoding PCR product. One clone (Os-1) was identified, among 300,000 recombinant plaques screened, and was found to contain a 3.6 kilobase (kb) cDNA insert (FIG. 4). Comparison of the deduced amino acid sequence of this clone with the sequence of furin/PACE revealed that it was missing approximately 200 amino acids from the amino-terminus.

Molecular Cloning of PACE 4 and 4.1 cDNAs and PACE 4 Gene

Subsequently, 300,000 recombinant plaques from a HepG2 cDNA library were probed with a 1.0 kb BglII DNA fragment derived from the 5' end of the Os-1 cDNA clone. This resulted in the isolation of two approximately full length clones with DNA inserts of 4.4 kb (clone L2—1) and 4.3 kb (clone L2—10).

Preliminary Northern blot analysis of several tissues and cell lines using the 1.0 kb Os-1 DNA probe identified a 4.4 kb MRNA transcript in most tissues (described below). In addition, the kidney cell line 293 revealed a mRNA of approximately 2.0 kb. The size of this transcript suggested that an alternative form of the PACE 4 protein existed since the MRNA size required to encode PACE 4 is 2.9 kb (FIG. 1). In an attempt to isolate this PACE 4 variant cDNA, termed PACE 4.1, a 293 cDNA library was constructed and 300,000 recombinant plaques were screened with the 1.0 kb Os-1 DNA probe. Several positive clones were identified including one that contained a cDNA insert of 1.7 kb (clone K-15). Preliminary DNA sequence analysis revealed that it was identical to PACE 4 at the 5' end but was lacking 270 bp encoding the amino-terminal 90 amino acids. DNA sequence analysis also revealed a unique 3' end on PACE 4.1 that was contained almost entirely on a 0.5 kb EcoRI DNA fragment (FIG. 5). Therefore, this unique PACE 4.1 EcoRI DNA fragment and an oligonucleotide probe complementary to the 5' end of PACE 4 were used to rescreen the 293 cDNA library. One clone was identified (K-1.1) that hybridized to both probes and was shown to contain a full-length cDNA insert of 1.9 kb.

Example 2

Structures of PACE 4 and 4.1 Deduced from CDNA Sequences

The full sequence of the PACE 4 cDNA (SEQ ID No: 1)and the encoded protein sequence (SEQ ID No: 2)are shown in FIG. 1. The encoded protein sequence is shown above that of the cDNA sequence; the numbering is based on the significant ORF in the cDNA. Likely active site residues are indicated by asterisks. Consensus sites for Asn-linked glycosylation are marked by diamonds and cysteine residues by bars. Potential dibasic proteolytic processing sites are indicated by arrows.

The coding sequence of PACE 4 contains three consensus sites for N-linked glycosylation and fifty-six cysteine residues. The active site, shown in the box in FIG. 1, includes a triad of amino acids: aspartate (Asp 205), histidine (His 246), and serine (Ser 420). A cysteine-rich region (CRR) is also present and, as shown in FIG. 1, is located in the vicinity of amino acid Cys 695 to amino acid Cys 965.

The translation of PACE 4 is most likely initiated at the ATG start codon shown (FIG. 1), since this is the only in-frame Met codon in the 5' region of the cDNA. In contrast to the amino-terminal sequence of furin/PACE, this Met is not followed immediately by a classical hydrophobic signal sequence. However, amino acids 43–63 of the large open reading frame resemble closely the proposed signal sequence for furin/PACE (Barr et al., 1991), including a predicted signal peptidase cleavage site following Ala63 (FIG. 1, arrowed) (von Heijne, 1986). The open reading frame encodes a PACE 4 precursor protein of 969 amino acids (SEQ ID No: 2) with a calculated molecular weight of 106.4 kD. As with KEX2 and its mammalian counterparts, PACE 4 contains a region of clustered basic residues immediately preceding the catalytic domain (FIG. 1). By direct comparison with the known cleavage sites for KEX2, PC2 and PC1/PC3 (Christie et al, 1991; Shennan et al., 1991) the Arg-Val-Lys-Arg motif at amino acids 146–149 most likely represents a propeptide cleavage junction, thereby making Gln150 the likely amino terminus of mature PACE 4.

The inferred sequence of PACE 4 contains three consensus sites for N-linked glycosylation and 56 Cys residues, with 44 of these Cys residues clustered in a carboxyl-terminal Cys-rich region analogous to, although somewhat longer than, that of furin/PACE. Again, in contrast to furin/PACE, which has a classical transmembrane domain, PACE 4 does not appear to possess such a region of hydrophobic amino acid residues for anchorage in cell membranes. Moreover, PACE 4 does not have a carboxyl-terminal amphipathic helix type anchor sequence proposed for PC2 and PC1/PC3 (Smeekens et al., 1991) and carboxypeptidase E (Fricker et al., 1990), thereby suggesting an alternate mode of subcellular localization for this enzyme.

The PACE 4.1 CDNA, isolated from the human kidney cell line, encodes a much smaller subtilisin-like protease with a termination codon introduced immediately subsequent to the catalytic domain and leading to a calculated molecular weight for PACE 4.1 of 53.3 kD (FIGS. 2B, 3). Truncation at this point removes a region of the molecule referred to as the P-domain. This region is similar to one which was identified in KEX2, and which has been shown to be essential for the activity of the yeast protease. The PACE 4.1 cDNA also contains a 3-untranslated region that is distinct from that of PACE 4 (FIG. 2), but is encoded by the 5'-cosmid clone PACE 4-COS 3. That alternate RNA splicing is occurring in this region can be inferred from the sequences of genomic clones isolated from this cosmid. For example, the sequence of a 620 bp PstI fragment from this cosmid encodes an exon (equivalent to exon 12 of furin/PACE (SEQ ID No: 5)) that clearly illustrates the intron/exon splice junction leading to either PACE 4 or PACE 4.1 (FIG. 3).

The unique CRR of PACE 4 comprises the C-terminal portion of the protein, including 44 cystine residues occurring between Cys 695 and Cys 965. The CRR apparently provides for localized interactions between PACE 4 and other cellular components, thereby modifying the activity of the enzyme.

The CRR domain is used to create novel fusion proteins by combining an oligonucleotide encoding the CRR with one encoding a functional domain of a heterologous protein. For example, a fusion protein having the catalytic domain of a different endoprotease and the CRR of PACE 4 is constructed by joining the appropriate DNA sequence coding for the endoprotease catalytic domain in reading frame with a DNA sequence encoding the CRR, and operatively inserted into an expression vector. The catalytic domain of PC2 provides proteolytic activity having altered specificity from that of natural PACE 4. DNA encoding PC2 is cleaved at a site 5' to the start codon and a site 3' to the region encoding the catalytic domain. PACE 4 clone L2—10 is cleaved with BglII and the C-terminal fragment including the CRR is isolated and ligated to the N-terminal DNA fragment from PC2. This construct is ligated into an expression vector. Expression of the construct in transformed cells yields a novel endoprotease having catalytic characteristics of PC2 and the cellular interactions of PACE 4.

Example 3

Similarity of PACE 4 to Other Dibasic Endoproteases

Comparisons of the sequence and structure of PACE 4 and PACE 4.1 with KEX2 and its mammalian homologs are illustrated in FIGS. 6 and 7. In addition to the conservation of spacing of the catalytic Asp, His, Asn (Asp), and Ser residues, also clearly apparent is the similarity in placement of the proposed processing site for removal of the propeptide region of each protease (FIG. 6). That this cleavage site is utilized has been demonstrated for KEX2 and for PC2 and PC1/PC3 (Christie et al., 1991; Shennan et al, 1991).

Amino acid sequence identities between the catalytic domain of PACE 4 and those of the previously described dibasic processing enzymes are shown in FIG. 7, and quantitated in Table 1.

TABLE 1

OVERALL % AMINO ACID SEQUENCE IDENTITIES BETWEEN THE CATALYTIC DOMAINS OF *SACCHAROMYCES CEREVISIAE* KEX2, AND THE MAMMALIAN PAIRED BASIC AMINO ACID RESIDUE CLEAVING ENZYMES

|  | yKEX2 | furin/PACE | PC2 | PC1/PC3 | PACE4 |
|---|---|---|---|---|---|
| yKEX2 (SEQ ID No: 7) | — | | | | |
| furin/PACE (SEQ ID No: 8) | 48 | — | | | |
| PC2 (SEQ ID No: 9) | 47 | 56 | — | | |
| PC1/PC3 (SEQ ID No: 10) | 49 | 65 | 57 | — | |
| PACE4 (SEQ ID No: 11) | 45 | 69 | 53 | 63 | — |

Example 4

Tissue Distribution of PACE 4 mRNA

To determine the tissue distribution of PACE 4 and PACE 4.1, northern blot analysis of poly(A)$^+$RNA from a variety of tissues and cell lines was carried out using cDNA probes specific to each transcript (FIG. 8 A–D).

Northern Blot Analysis

Multipl e tissue Northern (MTN) blots (panels A and B, FIG. 8) containing poly(A)$^+$RNA (2 µg) from human heart (lane 1), brain (lane 2), placenta (lane 3), lung (lane 4), liver (lane 5), skeletal muscle (lane 6), kidney (lane 7) and pancreas (lane 8) were pur chas ed from Clontech (Palo Alto, Calif.). Poly(A)$^+$RNA (2 µg) (panels C and D) from hamster insulinoma cell line HIT-15 (lane 9), human embryonic kidney cell line 293 (lane 10), human hepatoma cell line HEP G2 (lane 11), human umbilical vein endothelial cells (lane 12), human monocyte cell line U937 (lane 13), human lymphoblastoid cell line UC-729-6 (lane 14), and human osteosarcoma tissue (lane 15) were fractionated on 1.4% agarose gels in the presence of formaldehyde (Lehrach et al, 1977) transferred directly to nitrocellulose and processed as described (Thomas, 1980). Blots were hybridized with a PACE 4 specific probe (panels A and C) or a PACE 4.1 specific probe (panels B and D). Hybridization and washing conditions were as described above for the screening of cDNA libraries using cDNA probes.

A single PACE 4 4.4 kb transcript was seen at various levels in all tissues and cell lines tested (FIG. 8 A and C). This is similar to the widespread tissue distribution found with furin/PACE (Schalken et al., 1987; Barr et al., 1991) and is in contrast to the limited neuroendocrine tissue distribution of PC2 and PC3 transcripts (Smeekens and Steiner, 1990; Seidah et al., 1990; Smeekens et al, 1991). However, the 2.0 kb PACE 4.1 transcript was seen only in the 293 kidney cell line from which it was originally isolated (FIG. 8 B and D). The lack of the 2.0 kb PACE 4.1 transcript in all tissues tested suggests that it may represent an alternatively spliced PACE 4 transcript limited to certain cell types.

IV. Deposit of Biological Material

*Escherichia coli* strain HB101 host cells transformed with pAB23BXN-PACE 4 was deposited on Oct. 11, 1991, with the American Type Culture Collection (ATCC), Rockville, Md. (now Manassas, Va.), and designated as ATCC 68804. This deposit will be maintained under the terms of the Budapest Treaty on the International Recognition of the Deposit of Micro-organisms for purposes of patent procedure.

This deposit is provided merely as convenience to those of skill in the art, and is not an admission that a deposit is required under 35 U.S.C. § 112. The nucleic acid sequence of this plasmid, as well as the amino acid sequence of the polypeptide encoded thereby, are incorporated herein by reference and are controlling in the event of any conflict with the description herein. A license may be required to make, use, or sell the deposited material, and no such license is hereby granted.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A cell comprising a recombinant polynucleotide encoding a PACE 4 polypeptide selected from the group of:
   (a) natural-sequence PACE 4 having the amino acid sequence in FIG. 1 (SEQ ID No.2),
   (b) the mature PACE 4 polypeptide of (a),
   (c) a polypeptide fragment of (a) or (b) having the catalytic specificity of natural-sequence PACE 4 having the amino acid sequence of FIG. 1 (SEQ ID No.2), and
   (d) a mutant of (a) or (b) having the catalytic specificity of natural-sequence PACE 4 having the amino acid sequence of FIG. 1 (SEQ ID No. 2), wherein said mutant differs from the corresponding region of the sequence of FIG. 1 (SEQ ID NO: 2) at no more than 20% of the amino acid residues, wherein said cell is capable of expressing said PACE 4 polypeptide.

2. A cell comprising
   1) a polynucleotide encoding a PACE 4 polypeptide selected from the group of:
      (a) natural-sequence PACE 4 having the amino acid sequence in FIG. 1 (SEQ ID No.2),
      (b) the mature PACE 4 polypeptide of (a),
      (c) a polypeptide fragment of (a) or (b) having the catalytic specificity of natural-sequence PACE 4 having the amino acid sequence of FIG. 1 (SEQ ID No.2), and
      (d) a mutant of (a) or (b) having the catalytic specificity of natural-sequence PACE 4 having the amino acid sequence of FIG. 1 (SEQ ID No. 2), wherein said mutant differs from the corresponding region of the sequence of FIG. 1 (SEQ ID NO: 2) at no more than 20% of the amino acid residues, and
   2) a heterologous polynucleotide encoding a precursor polypeptide, wherein said precursor polypeptide is a substrate for PACE 4,
   wherein said cell is capable of expressing said PACE 4 polypeptide and said precursor polypeptide.

3. A method for producing a recombinant PACE 4 polypeptide, comprising:
   (a) providing a cell according to claim 1 and
   (b) incubating said cell under conditions that allow expression of said recombinant PACE 4 polypeptide.

4. A method for producing a desired mature polypeptide comprising incubating the cell of claim 2 under conditions that allow the expression of said PACE 4 polypeptide and expression and processing of said precursor polypeptide.

5. The method of claim 4, wherein said PACE 4 polypeptide is selected from the group of:
    (a) natural-sequence PACE 4 having the amino acid sequence in FIG. 1 (SEQ ID No.2), and
    (b) the mature PACE 4 polypeptide of (a).

6. The method of claim 4, wherein said PACE 4 polypeptide is a polypeptide fragment of (a) or (b) having the catalytic specificity of natural-sequence PACE 4 having the amino acid sequence of FIG. 1 (SEQ ID No.2).

7. The method of claim 4, wherein said PACE 4 polypeptide is a mutant of (a) or (b) having the catalytic specificity of natural-sequence PACE 4 having the amino acid sequence of FIG. 1 (SEQ ID No. 2), wherein said mutant differs from the corresponding region of the sequence of FIG. 1 (SEQ ID NO: 2) at no more than 20% of the amino acid residues.

8. The method of claim 4, wherein said PACE 4 polypeptide is a mutant of (a) or (b) having the catalytic specificity of natural-sequence PACE 4 having the amino acid sequence of FIG. 1 (SEQ ID No. 2), wherein said mutant differs from the corresponding region of the sequence of FIG. 1 (SEQ ID NO: 2) at no more than 10% of the amino acid residues.

9. The method of claim 4, wherein said PACE 4 polypeptide is a mutant of (a) or (b) having the catalytic specificity of natural-sequence PACE 4 having the amino acid sequence of FIG. 1 (SEQ ID No. 2), wherein said mutant differs from the corresponding region of the sequence of FIG. 1 (SEQ ID NO: 2) at no more than 5% of the amino acid residues.

10. The method of claim 4, wherein said cell is a mammalian cell.

11. The method of claim 4, wherein said cell is an insect cell.

12. The method of claim 4, wherein said cell is a microorganism selected from the group consisting of bacteria and fungi.

13. The method of claim 5, wherein said cell is a CHO cell.

14. The method of claim 5, wherein said cell is an insect cell selected from the group consisting of *Aedes aegypti, Autographa californica, Bombyx mori, Drosophila melanogaster, Spodoptera frugiperda* and *Trichoplusia ni*.

15. The method of claim 5, wherein said cell is a yeast cell.

16. A cell comprising a recombinant polynucleotide encoding a PACE 4.1 polypeptide selected from the group of:
    (a) the RNA splice mutant of natural-sequence PACE 4, having an amino acid sequence identical to that of Met 1 through Lys 471 of natural-sequence PACE 4 (SEQ ID No. 2), immediately followed by an amino acid sequence identical to that of Gly 4 through Val 19 of SEQ ID No.4,
    (b) a polypeptide fragment of (a) having the catalytic specificity of (a), and
    (c) a mutant of (a) having the catalytic specificity of (a), wherein said mutant differs from (a) at no more than 20% of the amino acid residues,
wherein said cell is capable of expressing said PACE 4.1 polypeptide.

17. A cell comprising
    1) a polynucleotide encoding a PACE 4.1 polypeptide selected from the group of:
        (a) the RNA splice mutant of natural-sequence PACE 4, having an amino acid sequence identical to that of Met 1 through Lys 471 of natural-sequence PACE 4 (SEQ ID No. 2), immediately followed by an amino acid sequence identical to that of Gly 4 through Val 19 of SEQ ID No.4,
        (b) a polypeptide fiagment of (a) having the catalytic specificity of (a), and
        (c) a mutant of (a) having the catalytic specificity of (a), wherein said mutant differs from (a) at no more than 20% of the amino acid residues, and
    2) a heterologous polynucleotide encoding a precursor polypeptide, wherein said precursor polypeptide is a substrate for PACE 4. 1,
wherein said cell is capable of expressing said PACE 4.1 and said precursor polypeptide.

18. A method for producing a recombinant PACE 4.1 polypeptide, comprising:
    (a) providing a cell according to claim 16 and
    (b) incubating said cell under conditions that allow expression of said recombinant PACE 4.1 polypeptide.

19. A method for producing a desired mature polypeptide comprising incubating the cell of claim 17 under conditions that allow the expression of said PACE 4.1 polypeptide and expression and processing of said precursor polypeptide.

20. The method of claim 19, wherein said PACE 4.1 polypeptide is the RNA splice mutant of natural-sequence PACE 4, having an amino acid sequence identical to that of Met 1 through Lys 471 of natural-sequence PACE 4 (SEQ ID No. 2), immediately followed by an amino acid sequence identical to that of Gly 4 through Val 19 of SEQ ID No.4.

21. The method of claim 19, wherein said PACE 4.1 polypeptide is a polypeptide fragment of (a) having the catalytic specificity of (a).

22. The method of claim 19, wherein said PACE 4.1 polypeptide is a mutant of (a) having the catalytic specificity of (a), wherein said mutant differs from (a) at no more than 20% of the amino acid residues.

23. The method of claim 19, wherein said PACE 4.1 polypeptide is a mutant of (a) having the catalytic specificity of (a), wherein said mutant differs from (a) at no more than 10% of the amino acid residues.

24. The method of claim 19, wherein said PACE 4.1 polypeptide is a mutant of (a) having the catalytic specificity of (a), wherein said mutant differs from (a) at no more than 5% of the amino acid residues.

25. The method of claim 19, wherein said cell is a mammalian cell.

26. The method of claim 19, wherein said cell is an insect cell.

27. The method of claim 19, wherein said cell is a microorganism selected from the group consisting of bacteria and fungi.

28. The method of claim 20, wherein said cell is a CHO cell.

29. The method of claim 20, wherein said cell is an insect cell selected from the group consisting of Aedes aegypti, Autographa californica, Bombyx mor, Drosophila melanogaster, Spodopterafrugiperda and Trichoplusia ni.

30. The method of claim 20, wherein said cell is a yeast cell.

* * * * *